(12) United States Patent
Young et al.

(10) Patent No.: US 8,706,537 B1
(45) Date of Patent: Apr. 22, 2014

(54) REMOTE CLINICAL STUDY SITE MONITORING AND DATA QUALITY SCORING

(71) Applicant: Medidata Solutions, Inc., New York, NY (US)

(72) Inventors: Stephen Young, Glenmoore, PA (US); Vincent Marinelli, Collegeville, PA (US); Mladen Laudanovic, New York, NY (US); Anson Kring, Royersford, PA (US); Andrew Kopelman, New York, NY (US)

(73) Assignee: Medidata Solutions, Inc., New York, NY (US)

( * ) Notice: Subject to any disclaimer, the term of this patent is extended or adjusted under 35 U.S.C. 154(b) by 0 days.

(21) Appl. No.: 13/679,533

(22) Filed: Nov. 16, 2012

(51) Int. Cl.
*G06Q 10/00* (2012.01)

(52) U.S. Cl.
USPC .......................................................... 705/7.11

(58) Field of Classification Search
USPC ................................................. 705/7.41, 7.39
See application file for complete search history.

(56) References Cited

U.S. PATENT DOCUMENTS

| | | | | |
|---|---|---|---|---|
| 6,353,767 B1* | 3/2002 | Wakeman et al. | ............... | 700/91 |
| 6,496,827 B2 | 12/2002 | Kozam | | |
| 6,856,973 B1* | 2/2005 | Bott | ............................ | 705/36 R |
| 6,879,970 B2* | 4/2005 | Shiffman et al. | ............... | 706/21 |
| 6,912,502 B1* | 6/2005 | Buddle et al. | ................. | 705/7.41 |
| 7,006,992 B1* | 2/2006 | Packwood | ....................... | 705/38 |
| 7,054,823 B1* | 5/2006 | Briegs et al. | ....................... | 705/2 |
| 7,213,037 B2* | 5/2007 | Rangadass | ............................. | 1/1 |
| 7,251,609 B1* | 7/2007 | McAlindon et al. | ............... | 705/3 |
| 7,353,238 B1* | 4/2008 | Gliklich | ................................. | 1/1 |
| 7,359,865 B1* | 4/2008 | Connor et al. | ............... | 705/7.28 |
| 7,386,466 B2* | 6/2008 | McLean et al. | ............... | 705/7.39 |
| 7,409,357 B2* | 8/2008 | Schaf et al. | .................. | 705/7.28 |
| 7,415,447 B2* | 8/2008 | Shiffman et al. | ............... | 706/47 |
| 7,441,197 B2* | 10/2008 | Tschiegg et al. | ............... | 715/741 |
| 7,483,917 B2* | 1/2009 | Sullivan et al. | ....................... | 1/1 |
| 7,536,405 B2* | 5/2009 | Tschiegg et al. | ....................... | 1/1 |
| 7,571,109 B2* | 8/2009 | Fawls et al. | .................. | 705/7.28 |
| 7,606,795 B2* | 10/2009 | Hsu et al. | ................................. | 1/1 |
| 7,644,026 B2* | 1/2010 | Cohen et al. | ................. | 705/36 R |
| 7,698,148 B2* | 4/2010 | Lavu et al. | ...................... | 705/1.1 |
| 7,711,670 B2* | 5/2010 | Roediger | ......................... | 706/46 |
| 7,752,057 B2* | 7/2010 | Ikeguchi et al. | .................. | 705/2 |
| 7,853,476 B2* | 12/2010 | Reiner | .............................. | 705/2 |
| 7,921,125 B1* | 4/2011 | Houriet et al. | ................ | 707/754 |

(Continued)

OTHER PUBLICATIONS

Highlights of the People Risk Index Ratings Aon Consulting, 2010.*

(Continued)

*Primary Examiner* — Scott L Jarrett
(74) *Attorney, Agent, or Firm* — Mayer Brown LLP; Robert Greenfeld

(57) ABSTRACT

A method for remote site monitoring includes receiving data from a data site, converting those data into a site-level quality score using a metric risk profile, and calculating a risk indicator based on the site-level quality score. The metric risk profile may be based on historic data and study data, where the study data is received from a plurality of data sites. In some embodiments, converting the data includes normalizing a value of a metric by applying to it the metric risk profile and aggregating the normalized metric values to calculate the site-level quality score. An apparatus for remote site monitoring is also described.

29 Claims, 11 Drawing Sheets

(56) References Cited

U.S. PATENT DOCUMENTS

| | | | |
|---|---|---|---|
| 7,937,423 B2* | 5/2011 | Schneider | 705/2 |
| 8,086,708 B2* | 12/2011 | Breitgand et al. | 709/223 |
| 8,140,383 B2* | 3/2012 | Busch | 705/7.38 |
| 8,180,710 B2* | 5/2012 | Strichman et al. | 705/400 |
| 8,185,430 B2* | 5/2012 | Edwards et al. | 705/7.28 |
| 8,423,388 B1* | 4/2013 | Galusha et al. | 705/4 |
| 8,515,774 B2* | 8/2013 | Abraham-Fuchs et al. | 705/2 |
| 2002/0078175 A1* | 6/2002 | Wallace et al. | 709/219 |
| 2002/0128861 A1 | 9/2002 | Lau et al. | |
| 2003/0014287 A1* | 1/2003 | Williams et al. | 705/7 |
| 2004/0064341 A1 | 4/2004 | Langan et al. | |
| 2004/0064346 A1* | 4/2004 | Schneider et al. | 705/4 |
| 2004/0122756 A1* | 6/2004 | Creeden et al. | 705/35 |
| 2004/0210574 A1* | 10/2004 | Aponte et al. | 707/5 |
| 2005/0154628 A1* | 7/2005 | Eckart et al. | 705/10 |
| 2005/0182658 A1* | 8/2005 | Abraham-Fuchs et al. | 705/2 |
| 2005/0182663 A1* | 8/2005 | Abraham-Fuchs et al. | 705/3 |
| 2005/0192963 A1* | 9/2005 | Tschiegg et al. | 707/9 |
| 2005/0256380 A1* | 11/2005 | Nourie et al. | 600/300 |
| 2006/0161456 A1* | 7/2006 | Baker et al. | 705/2 |
| 2006/0287997 A1 | 12/2006 | Rugh | |
| 2007/0016542 A1* | 1/2007 | Rosauer et al. | 706/21 |
| 2007/0061393 A1* | 3/2007 | Moore | 709/201 |
| 2007/0150313 A1* | 6/2007 | Abraham-Fuchs et al. | 705/3 |
| 2008/0077457 A1* | 3/2008 | Pannatier et al. | 705/7 |
| 2008/0140514 A1* | 6/2008 | Stenger | 705/10 |
| 2008/0154637 A1 | 6/2008 | Capelli et al. | |
| 2008/0270181 A1* | 10/2008 | Rosenberg | 705/2 |
| 2008/0270420 A1 | 10/2008 | Rosenberg | |
| 2008/0319726 A1* | 12/2008 | Berge et al. | 703/10 |
| 2009/0138306 A1* | 5/2009 | Coburn et al. | 705/7 |
| 2009/0276259 A1* | 11/2009 | Bliznak | 705/7 |
| 2010/0198630 A1* | 8/2010 | Page et al. | 705/7 |
| 2010/0324936 A1 | 12/2010 | Vishnubhatla et al. | |
| 2011/0077958 A1 | 3/2011 | Breitenstein et al. | |
| 2011/0161245 A1* | 6/2011 | Hollas | 705/36 R |
| 2011/0191138 A1* | 8/2011 | Saraf | 705/7.28 |
| 2011/0313782 A1* | 12/2011 | DeMeyer et al. | 705/2 |
| 2012/0053995 A1* | 3/2012 | D'Albis et al. | 705/7.39 |
| 2012/0096005 A1* | 4/2012 | O'Connor | 707/741 |
| 2012/0150570 A1* | 6/2012 | Samad-Khan et al. | 705/4 |
| 2012/0226621 A1* | 9/2012 | Petran et al. | 705/317 |
| 2012/0296695 A1* | 11/2012 | McGill et al. | 705/7.28 |
| 2012/0323589 A1* | 12/2012 | Udani | 705/2 |
| 2013/0013332 A1 | 1/2013 | Frieder et al. | |
| 2013/0060599 A1* | 3/2013 | Jinfeng et al. | 705/7.28 |
| 2013/0179314 A1* | 7/2013 | Stoke et al. | 705/31 |
| 2013/0311196 A1 | 11/2013 | Fay et al. | |

OTHER PUBLICATIONS

Cleveland, David, Country Risk Maps Jun. 2007.*
Ergometrics.com—web pages Ergometrics, Mar. 2000, Retrieved from Archive.org, Jan. 25, 2007.*
INC Research Leads the Way for Risk-Based Monitoring Using Medidata Targeted SDV Solution Medidata, Dec. 2012.*
Nordic Bioscience Targets 20% SDV with Risk-Based Monitoring to Streamline Clinical Trial Execution Medidata, Aug. 2012.*
Miller, George, Risk approach comes to site monitoring FierceBiotechIT, Aug. 30, 2010.*
Venet, David et al., A statistical approach to central monitoring of data quality in clinical trials Clinical Trials, Jun. 8, 2012.*
Lawton, Andy et al., Risk Based Approach—Case Study FDA meeting Quality by Design, Aug. 2011.*
Elsa, Valdes-Marquez et al., A key risk indicator approach to central statistical monitoring in multicentre clinical trials: method development in the context of an ongoing large-scale randomized trial, Clinical Trials Methdology Conference, Oct. 2011.*
Cochran, Crissy J. et al., Oversight of Clinical Investigations: A Risk-Based Approach to Monitoring (Draft Guidance) U.S. Food and Drug Administration, Oct. 2011.*
Williams, G.W., The other side of clinical trial monitoring; assuring data quality and procedural adherence Clinical Trials, vol. 3, No. 6, 2006.*
Baigent C. et al., Ensuring trial validity by data quality assurance and diversification of monitoring methods Clinical Trials, vol. 5, No. 1, 2008.*
De, Sourabh, Hybrid approaches to clinical trial monitoring: Practical alternatives to 100% source data verification, Perspectives Clinical Research, vol. 2, No. 3, Jul.-Sep. 2011.*
Nelson, Greg, Implementing Metrics Management for Improving Clinical Trials Performance BeyeNetwork, Jul. 17, 2008.*
Doffange, Erik, Implementation of Key Risk Indicators for a large scale trial PhUSE Single Day Events, Apr. 28, 2011.*
Workshop on Quality Risk Management: Making Clinical Trials Fir for Purpose: Summar of Meeting held Aug. 23-24, 2011 Clinical Trials Transformation Initiative, Feb. 2012.*
Cognizant's Clinical Transformation: More than a solution, It's a New Way to Work Cognizant, Jul. 2012.*
Risk-based Monitoring Strategies for Improved Clinical Trial Performance Cognizant, 2013.*
Widler, Beat, Principles of Quality Risk Management—Session I: Principles for Building Quality into Clinical Trial Development, Aug. 2011.*
Green, Jeanne et al., MCC Update: Implementing Standardized Clinical Trial Performance Metrics to Manage Risk and Drive Quality in Clinical Trials, Metrics Champion Consortium, Third Annual Effective Business Development Outsourcing Relationships, Jul. 20, 2011.*
Risk-Adapted Monitoring in Clinical Tirals European Clinical Research Infrastracture Network, 2011.*
Getting the Pulse on the Industry: Soundbites from Medidata User Group, Geeks Talk Clinical Blog, May 18, 2012 (http://blog.mdsol.com/2012/05/18/getting-the-pulse-on-the-industry-soundbites-from-medidata-user-group/, last accessed on Nov. 14, 2012).
Guidance for Industry: Oversight of Clinical Investigations—A Risk-Based Approach to Monitoring (Draft Guidance), Aug. 24, 2011, U.S. Department of Health and Human Services, Food and Drug Administration, United States (http://www.fda.gov/downloads/Drugs/.../Guidances/UCM269919.pdf, last accessed on Nov. 16, 2012).
Guidance for Industry: E6 Good Clinical Practice: Consolidated Guidance, Apr. 1996, International Conference on Harmonisation of Technical Requirements for Registration of Pharmaceuticals for Human Use (ICH), U.S. Department of Health and Human Services, Food and Drug Administration, United States (http://www.fda.gov/downloads/Drugs/.../Guidances/ucm073122.pdf, last accessed on Nov. 16, 2012).
ICH Topic E6 (R1)—Guideline for Good Clinical Practice, Step 5, Note for Guidance on Good Clinical Practice (CPMP/ICH/135/95), Jul. 2002, European Medicines Agency, London, United Kingdom.
ICH Harmonised Tripartite Guideline—Statistical Principles for Clinical Trials E9, Current Step 4 version, Feb. 5, 1998, International Conference on Harmonisation of Technical Requirements for Registration of Pharmaceuticals for Human Use.
Dunham, Corey et al., Implementation of Adaptive Clinical Trials, an Aptiv Solutions White Paper, Mar. 14, 2012, Aptiv Solutions.
Henderson, Lisa, Have Monitor, Will Travel?, Applied Clinical Trials Online, Jun. 8, 2010 (http://www.appliedclinicaltrialsonline.com/appliedclinicaltrials/News/Have-Monitor-Will-Travel/ArticleStandard/Article/detail/672687, last accessed on Nov. 14, 2012).
Tantsyura, Vadim, Who's Afraid of Risk-Based Monitoring?, Geeks Talk Clinical Blog, Sep. 21, 2012 (http://blog.mdsol.com/2012/09/21/whos-afraid-of-risk-based-monitoring/, last accessed on Nov. 16, 2012).
Tantsyura, Vadim et al., Risk-based Source Data Verification Approaches: Pros and Cons, Drug Information Journal, Nov. 8, 2010, vol. 44, pp. 745-756, Drug Information Association, Inc.
Notes from presentation given by Stephen Young at Sapphire Now Conference, May 2011.
Young, Steve; Baur, Trent; & Pines, Josh, Medidata Insights Product Webinar, Jul. 21, 2011.
Young, Steve & Pines, Josh, Medidata Insights Product Webinar, Oct. 19, 2011.
Halloran, Laurie & Young, Steve, New Approaches to Site Monitoring and Management, May 23, 2012.

(56) References Cited

OTHER PUBLICATIONS

Young, Steve, Risk-Based Site Monitoring & Data Management's Role, Sep. 2012.
Young, Steve, Site Quality Management and Risk-Based Monitoring—A New Approach, Nov. 12, 2012.
Young, Steve & Altman, Igor, Using the Medidata Clinical Cloud to Implement TransCelerate's Risk-Based Monitoring Methodology, Jul. 30, 2013.
Young, Steve, Solutions to Enable and Optimize Strategic Monitoring, Sep. 25, 2013.
Petrarca, Mike, Ganguly, Shantanu, Ph.D.; & Young, Steve, How to be Confident Your Risk-Based Monitoring Program is Working, Sep. 26, 2013.
Young, Steve & Given, Kyle, Risk-Based Monitoring: Implementation Success Stories, Oct. 9, 2013.
Young, Steve, Using Analytics & Benchmarking to Optimize Targeted Site Monitoring, Dec. 9, 2011.
Young, Steve, Enabling Targeted Monitoring with a Centralized Site Quality Management Program, Apr. 11, 2012.
Young, Steve, Leveraging Clinical Development Metrics—Focus on Site Quality, Apr. 26, 2012.
Young, Steve, Turning Clinical R&D Metrics and Analytics into Transformational Solutions, CORE 2012, Oct. 11, 2012.
Young, Steve, Medidata Case Study: The Key Initiatives of the Insights Council, PCT 2012, Nov. 7, 2012.
Young, Steve, Best Practices for Centralized Site Quality Monitoring, Nov. 15, 2012.
Young, Steve, Optimizing Monitoring Through Site Quality Management, 9th Annual Clinical Performance Metrics and Benchmarking Summit, Dec. 8, 2012, Philadelphia, PA.
Young, Steve, Risk-Based Monitoring: Right Sizing SDV Without Compromising Quality, ACRP 2013 Global Conference & Exhibition, Apr. 13, 2013, Orlando, FL.
Young, Steve, Centralized Site Quality Management—Best Practices & Implications for Data Management, SCDM 2013 Annual Conference, Sep. 10-13, 2013, Chicago, IL.
Young, Steve, Solutions to Enable a Successful Risk-Based Monitoring Implementation, Oct. 24, 2013.
Young, Stephen & Mundra, Ashwin, Data Quality Monitoring, European Pharmaceutical Contractor, Autumn 2010.
Mundra, Ashwin & Young, Stephen, Are You Properly Equipped to Execute Risk-Based Site Monitoring?, PharmaVOICE, Nov. /Dec. 2010.
Young, Stephen, Enable Risk-based Site Monitoring, Medidata Rave® Targeted SDV, Aug. 2011, Medidata Solutions, Inc.
Young, Steve, Site Quality Management—Product Preview, Jun. 6, 2012.
Young, Stephen, Nordic Bioscience Targets 20% SDV with Risk-Based Monitoring to Streamline Clinical Trial Execution, Case Study, Aug. 2012, Medidata Solutions, Inc.
Young, Stephen, Adopting Site Quality Management to Optimize Risk-Based Monitoring, White Paper, Oct. 2012, Medidata Solutions, Inc.
Young, Stephen, INC Research Leads the Way for Risk-Based Monitoring Using Medidata Targeted SDV Solution, Case Study, Dec. 2012, Medidata Solutions, Inc.
Young, Stephen, Medidata Insights™ SQM Improve Site Quality With a Turnkey, Centralized Monitoring Solution, Nov. 2013, Medidata Solutions, Inc.
Written opinion of the International Searching Authority, PCT/US2013/70138, Jan. 16, 2014.

* cited by examiner

US 8,706,537 B1

REMOTE CLINICAL STUDY SITE MONITORING AND DATA QUALITY SCORING

BACKGROUND

Distributed systems exist that consist of a number of similar sites geographically distributed that perform similar types of tasks. Examples of these systems are franchise systems, sales offices of a company, and clinical drug trials. It may be desirable to monitor data generated at these sites to ensure uniformity of operation and integrity of the data. Such quality monitoring may be performed on site or remotely.

Looking at clinical drug trials as an example of such distributed systems, in the United States and other countries, marketing approval for pharmaceuticals and medical devices typically requires testing on humans. Through the testing process, which includes clinical trials, clinical data concerning the safety, efficacy, as well as other critical attributes of the tested drug or device are typically collected for submission to the United States Food and Drug Administration (FDA) or other regulatory agency. In the United States alone, tens of thousands of clinical trials are run annually, involving millions of volunteers. These volunteers are generally tested at a variety of locations, known as clinical sites, and each site generates data regarding the drug or device under investigation as well as data regarding the testing process itself.

Because there are so many distributed test sites, the sites are generally monitored to ensure data integrity across the sites and the clinical trial. Because on-site monitoring of clinical trials, which usually entails traveling to each site numerous times, can use over 30% of a drug company's clinical trial budget, on-site monitoring represents one of the largest cost drivers in clinical research.

Figure 1:
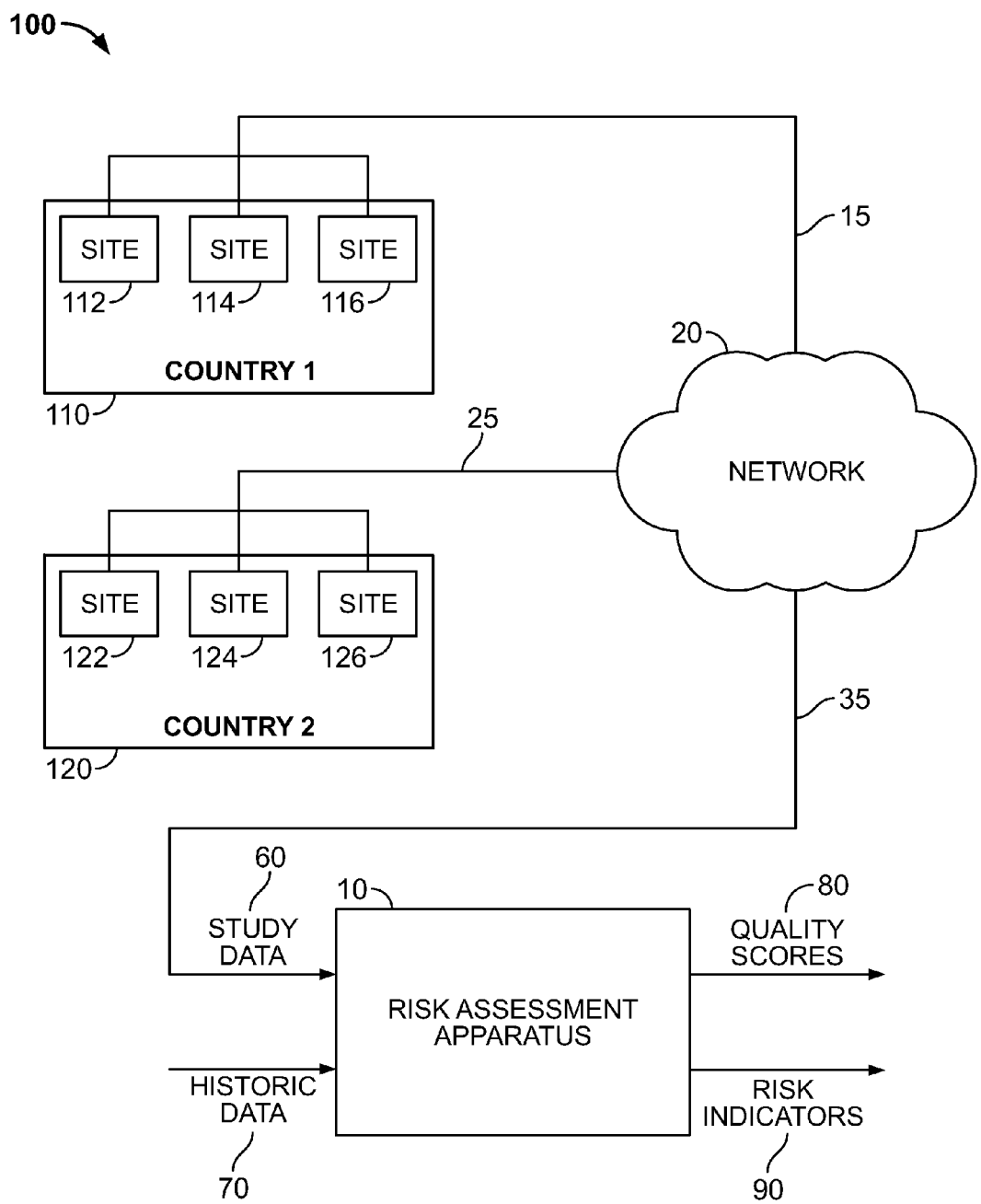
FIG. 1 is a block diagram of a system including a risk assessment apparatus according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Embodiments of the present invention may be used in a variety of applications. Although the present invention is not limited in this respect, the systems and methods disclosed herein may be used in or with clinical drug or device trials, monitoring of sales operations and associates, monitoring of retail services and locations, and other data-intensive applications in which users may desire to assess quickly the quality of data coming from a variety of sources. For example, it may be appreciated that the present invention could be utilized in sales, retail, or franchise organizations, wherein the quality of data generated by remote offices or individuals in compliance or conjunction with a centralized office or rules could be monitored or assessed.

A clinical trial (also called a clinical study, an interventional study, or, as used herein, a study or a trial) is typically directed to a specific therapeutic area, and may be categorized by phase. In a Phase I clinical study, the drug or device may be tested on approximately 20 to 100 volunteers (also known as patients or subjects) in order to gather clinical data on safety and dosage; in Phase II, clinical data may be gathered from approximately 100 to 500 volunteers in order to gather clinical data on efficacy and side-effects; and in Phase III, clinical data may be gathered from approximately 500 to 3000 or more volunteers in order to collect definitive evidence of safety and efficacy to obtain marketing approval of the drug or device.

A pharmaceutical company, an academic research center, a federal agency, or a clinical research center typically sponsors clinical trials. The Sponsor or its Contract Research Organization (CRO) (a person or an organization—commercial, academic, or other—contracted by the sponsor to perform one or more of a sponsor's trial-related duties and functions) generally selects the locations, known as Investigative Sites ("Sites"), at which the clinical study will be conducted. Sites typically can be hospitals, clinics, universities, doctors' offices, research institutions, or corporate trial locations. Over the course of a clinical study, the Principal Investigator ("PI") or other personnel at the Site are typically responsible for recording data, including information about the subjects and clinical data. Data captured by the PI or other site personnel are entered manually into case report forms (CRFs) or into electronic CRFs (eCRFs) hosted on electronic data capture (EDC) systems. However, clinical data collected for the purpose of the clinical trial is typically first recorded into a site-specific source such as a paper-based patient chart or electronic medical record system prior to being transcribed into the EDC system being utilized for the clinical trial. Such manual transcription may lead to accidental data errors. In addition, a Site may be fraudulently entering incorrect clinical data or otherwise deviating from good clinical practice or from the study protocol.

It is therefore desirable for Sponsors and CROs to ensure the integrity of the clinical trial data; they typically also ensure that the clinical study is being conducted in accordance with the clinical study's protocol, as well as with Good Clinical Practice (GCP) and other regulatory requirements. Through periodic in-person visits by personnel known as either Clinical Research Associates (CRAs) or Site Monitors, Sponsors and CROs typically also ensure the integrity of the clinical data being recorded and reported, as well as the protection of patient safety. Sponsors frequently spend thirty percent (30%) or more of their clinical trial budget for site monitoring activities.

In more detail, once a Site begins to recruit subjects, CRAs (or Site Monitors) typically conduct periodic monitoring visits in order to make sure that data have been entered correctly, that all relevant source data have been transcribed into the EDC system, and that data are supported by source data in a patient's chart. Such monitoring visits may involve several steps and processes. The CRA typically meets with the PI and study coordinator, reviews informed consent forms, conducts Source Data Verification (SDV), reviews CRFs/eCRFs, raises monitoring queries, reviews safety data (Adverse Events and Severe Adverse Events), collects CRFs (if the CRF is in paper form), identifies and documents protocol deviations and violations, reviews the site file, reviews drug supply and drug handling, reviews screening logs, and visits all departments involved with the study. The CRA may document the visit in a trip report, which is similar to an audit report. This report may then undergo a review and approval process with the CRA's manager. If the CRA works for a CRO, that CRO may consolidate completed visit reports on a periodic basis and submit them to the Sponsor.

Of all the tasks accomplished by the CRA, Source Data Verification (SDV) can be the most resource-intensive and costly. CRA verification of all CRF/eCRF data, known as 100% SDV, has been the industry norm, even though it is not required by current regulations. Current FDA Draft Guidance states that monitoring should include a mix of centralized monitoring (e.g., through the use of data checks, described below) and on-site monitoring. This mixed approach may reduce monitoring-related time and cost without compromising clinical data quality.

Several systems have been used to address the cost of monitoring and ensure the accuracy of the data. EDC systems, such as Medidata Solutions' Rave®, have the capability of automatically checking for certain data errors. For example, the EDC system can be set up to automatically flag improperly entered data, such as a non-numerical value in a field requiring a subject's age. Other systems, such as Medidata Solutions' Rave® Targeted Source Data Verification (TSDV) system, allow for the prioritization of critical data and/or the use of random sampling to pre-select data for SDV during on-site monitoring visits. For example, different blocks of clinical subjects may be assigned to different TSDV plans, whereby a first block of subjects could have all source data verified, but a second block of subjects would have less than 100% of their source data verified. The second block of subjects may require only the source data for certain data collection forms or fields verified, at the request of the administrator or planner of a clinical trial. Such systems may reduce monitoring requirements, but lack capabilities such as remote, centralized monitoring, which would further reduce the need for expensive on-site monitoring. This TSDV plan is static and would therefore remain in effect throughout the entirety of a study—in other words, the degree of SDV that every patient will undergo would be determined before a study begins. In contrast, in the dynamic, risk-based system of the present invention, emerging data from the study could be used to modify the degree of SDV to be performed on future patients. This determination would be based on measures of risk that are emerging for each site.

The inventors have realized that remote and central monitoring of one or more site-derived quality metrics can ensure high quality across all Sites in a clinical trial without incurring the traditionally high resource cost associated with 100% SDV. By associating those metrics with risk indicators, a Site or Sites with a higher likelihood (i.e., risk) of having quality issues in the conduct of the clinical trial can be identified proactively and the deficiency or deficiencies remediated. These deficiencies can be partially addressed through TSDV changes, as well as through less resource-intensive means than SDV, such as phone calls to sites to review and correct the deficient aspect of their trial conduct, etc.

To that end, embodiments of the invention include development of metrics concerning clinical trial conduct at the site level, and these metrics may be grouped, normalized, or aggregated in order to determine an associated risk level and to utilize such risk levels to determine associated site-level quality scores, in order to more quickly identify trends in the data and to identify areas, personnel, and/or organizations that may require more in-depth review. Other embodiments may aggregate site-level data geographically, such as at a city level, state level, regional level, country level, or worldwide study level (i.e., across all sites within a given study), or organizationally, such as by CRA or other grouping having a common element, in order to allow a Sponsor or CRO to quickly identify appropriate internal resources to address any identified quality issues.

An objective of these embodiments is to determine when a given site has deviated from a determined or expected range for a given quality metric by a degree that may indicate a significant quality issue. Another objective is to allow a user to measure and score the accuracy and trustworthiness of clinical trials performed at one or more clinical trial sites. Yet another objective is to provide a system of remote site data quality monitoring whereby a user of such system may be apprised of potential site data quality issues over varying periods of time, including near real-time.

Reference is now made to FIG. 1, which is a block diagram of a system 100 including a risk assessment apparatus 10, according to an embodiment of the present invention. System 100 may include a number of sites generating data and transferring such data over connections 15, 25 to network 20 and to risk assessment apparatus 10 over connection 35. Sites 112, 114, 116 and 122, 124, 126 may be located in various countries 110, 120 or other geographically distinct areas (or other groupings of sites having a common element). While three sites and two countries are illustrated in FIG. 1, the present invention contemplates the use of any number of sites in any number of countries. Network 20 may be any type of communications network, including a public or private telephone (e.g., cellular, public switched, etc.) network and/or a computer network, such as a LAN (local area network), a WAN (wide area network), or the Internet or an intranet, that facilitates risk assessment apparatus 10 to interact with the sites in order to send and receive data and other information. Connections 15, 25, and/or 35 may be wired or wireless connections or even a file transfer system, such as a CD, DVD, or thumb or flash drive, which contains data from the sites.

The data may be associated with a clinical trial for a drug or medical device, or may be any other type of data that can assess operation at a site, including but not limited to performance of sales associates at different locations or performance of retail locations, including franchises. As will be described in more detail below, risk assessment apparatus 10 may calculate one or more quality scores 80 and risk indicators 90 based on study data 60, received from the various sites, and historic or industry or other data 70 received from any source of data. Quality scores 80 and risk indicators 90 may then be used to evaluate each site, groupings of sites, or a study as a whole. Risk assessment apparatus 10 may be embodied on any type of computing program or application residing on any type of computing device, including but not limited to a personal, laptop, tablet, or mainframe computer, a mobile phone, or a personal digital assistant (PDA).

Figure 2A:
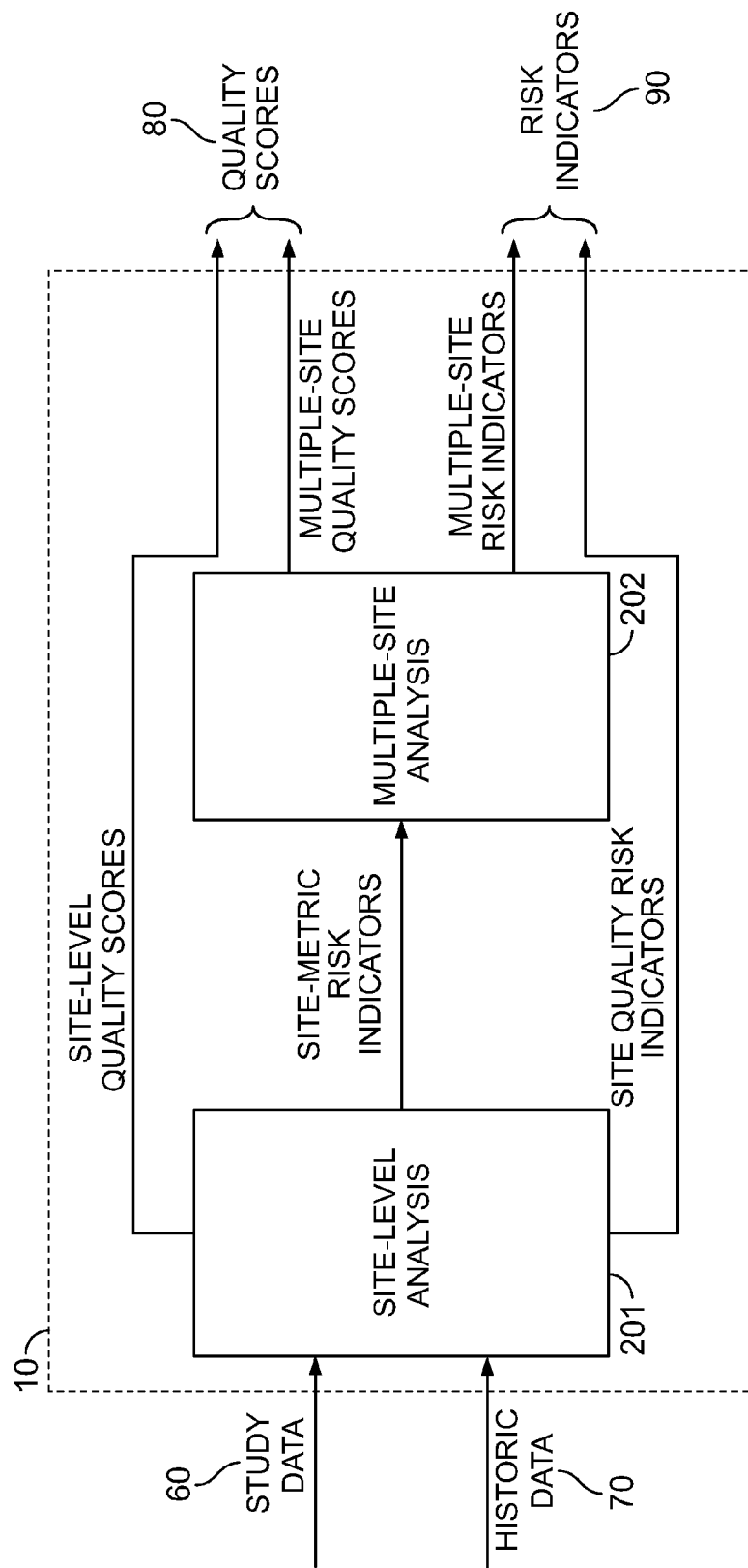
FIGS. 2A-2D are block diagrams showing operation of the risk assessment apparatus illustrated in FIG. 1.
Figure 2B:
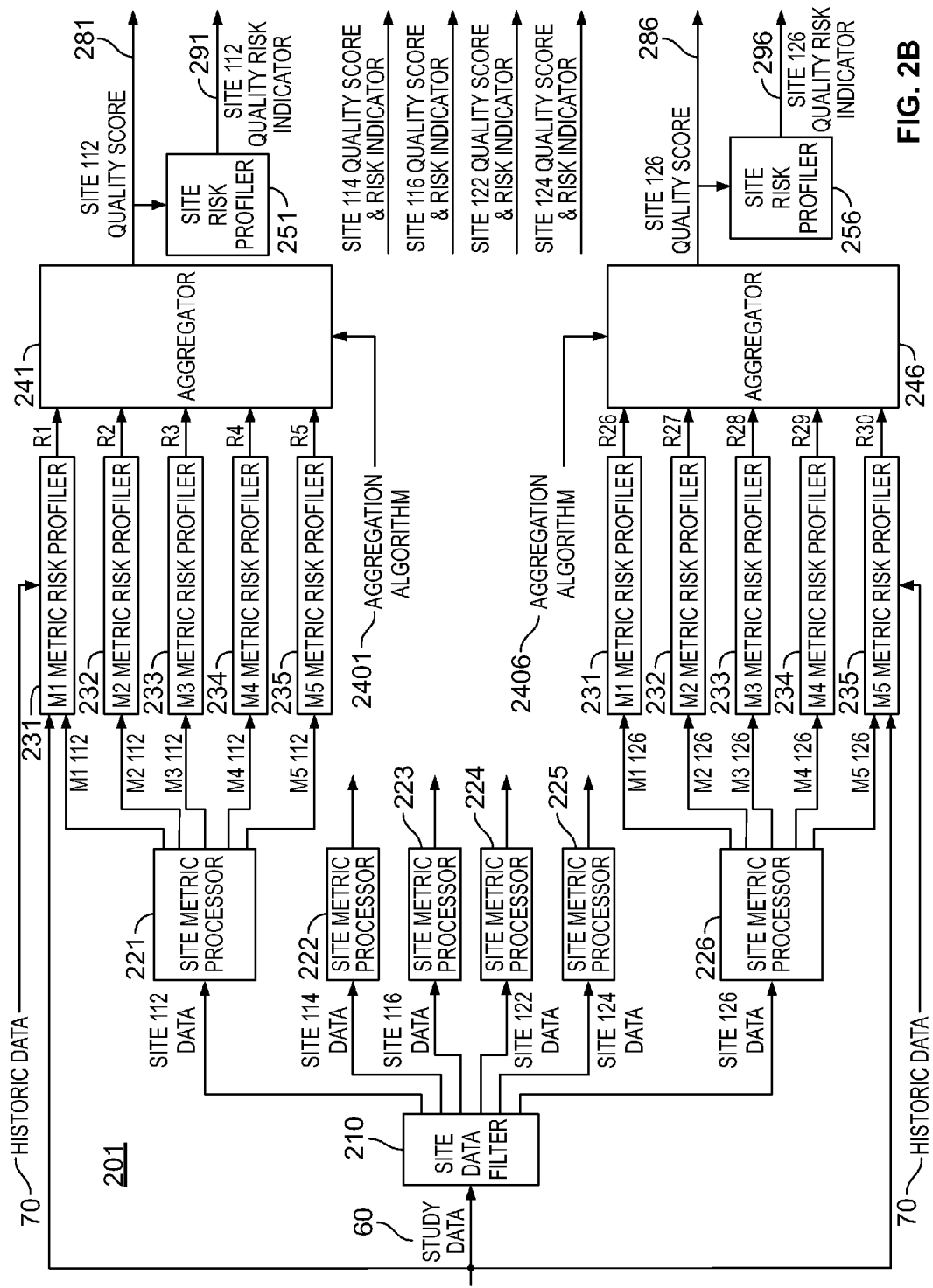
Figure 2C:
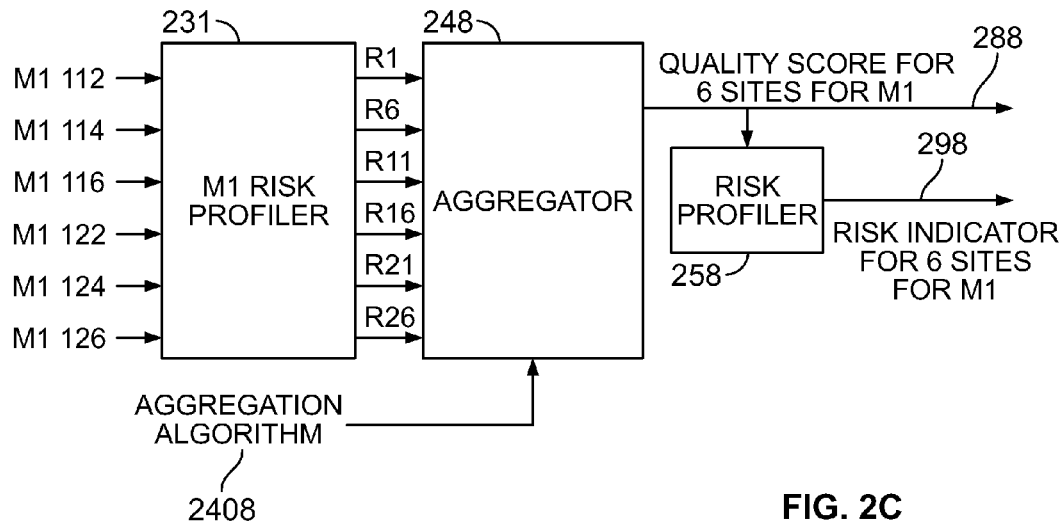
Figure 2D:
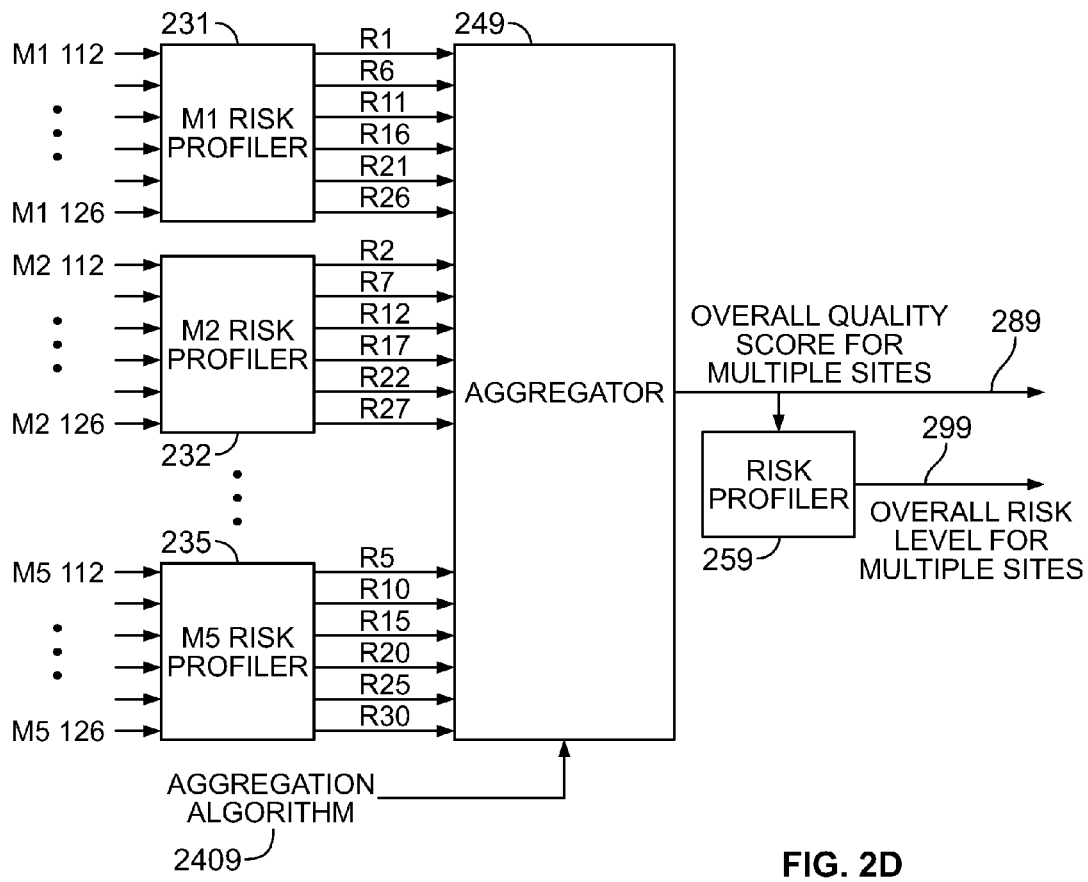

FIGS. 2A-2D are block diagrams illustrating the operation of risk assessment apparatus 10 in more detail. FIG. 2A illustrates the main system blocks of risk assessment apparatus 10, according to an embodiment of the present invention, FIG. 2B shows how site-level quality scores and risk indicators may be determined, according to an embodiment of the present invention, and FIGS. 2C and 2D show how quality scores and risk indicators above the site level may be determined, according to an embodiment of the present invention.

FIG. 2A shows site-level analysis block 201 and multiple-site analysis block 202. Site-level analysis block 201 may take study data 60 and historic data 70 and may determine site-level quality scores, site-metric risk indicators, and site quality risk indicators. Site-level analysis block 201 is partially schematically illustrated in FIG. 2B. Multiple-site analysis block 202 may take site-metric risk indicators from site-level analysis block 201 and may determine multiple-site quality scores and multiple-site risk indicators. Multiple-site analysis block 202 is partially schematically illustrated in FIGS. 2C and 2D.

In FIG. 2B, site-level analysis block 201 may include site data filter 210, site metric processors 221-226, metric risk profilers 231-235, aggregators 241-246, and site risk profilers 251-256. (For ease of readability of FIG. 2A, aggregators 242-245 and site risk profilers 252-255 are not shown.)

Site data filter 210 may take study data 60 and separate out data from each individual site, for example, into site 112 data, site 114 data, site 116 data, etc. Alternatively, site data filter 210 may not be included in site-level analysis block 201 if individual site data are separately communicated to risk assessment apparatus 10, for example, either directly from the sites themselves or via other transfer means such as CD, DVD, or thumb or flash drive.

Site metric processors 221-226 may take the individual site data and separate out the data to determine the values of each of one or more metrics for an individual site. Five metrics, Metric1 (M1), Metric2 (M2), etc., are shown in FIG. 2B. These metrics could be for any of a number of measures for which data is collected at the sites. In the case of a clinical trial, the metrics could include query rate, subject visit to entry cycle time, query response cycle time, screen failure rate, early termination rate, adverse event (AE) rate, severe adverse event (SAE) rate, protocol deviation rate, and/or visit schedule deviation rate, as well as other metrics which may be appreciated by a person of ordinary skill in the art. Although five metrics are shown in FIG. 2B, any number of metrics may be determined from the data and used in risk assessment apparatus 10.

Alternatively, site metric processors 221-226 may not be included in site-level analysis block 201 if individual site metric data or site metrics are separately communicated to risk assessment apparatus 10, for example, either directly from the sites themselves or via other transfer means such as CD, DVD, or thumb or flash drive.

The following provides an example of how site-level analysis block 201 may operate up to the point thus far described in the context of a clinical trial. Each site collects clinical data associated with the metrics listed above, for example blood pressure data, heart rate data, and metabolism data, as well as monitoring data, such as meta-data associated with the collection of clinical data or other data concerning the gathering or processing of clinical data. All of this data from all of the sites comprises study data 60 and are communicated to risk assessment apparatus 10. Site data filter 210 separates out the data for each site, for example, site 112 data, which may include the clinical data for site 112 as well as the monitoring data for that site. Site metric processor 221 takes the site 112 data, identifies the monitoring data, and separates out the data that will correspond to each metric M1-M5, such as the number of queries, the times for subject visit to entry cycle, the query response cycle times, the number of screen failures, and the number of early terminations. Site metric processor 221 then calculates values of metrics M1-M5, e.g., query rate, mean subject visit to entry cycle time, mean query response cycle time, screen failure rate, and early termination rate, using the separated site data. The values of metrics M1-M5 for site 112, denoted by M1 112, M2 112, etc., may be single numbers or other values that are then available to metric risk profilers 231-235.

Each metric risk profiler 231-235 receives a value associated with metrics M1-M5 and, using a metric risk profile which is typically specific to each metric risk profiler 231-235, may calculate or normalize or categorize the metric into a site-metric risk indicator, e.g., R1-R30 (metric risk indicators R6-R25 are not shown in FIG. 2B). It is also possible that the same metric risk profile is applied to more than one metric risk profiler. Typically, there will be a specific quantity of predetermined site-metric risk indicator designations. In one embodiment, there may be three site-metric risk indicator designations, e.g., low (L), medium (M), and high (H). If the embodiment also includes visual indicators of risk, low, medium, and high indicators may be indicated by colors, for example by green, yellow, and red, respectively. Continuing the above example, the values of metrics M1 through M5 for each site may be converted to an L, M, or H based on the metric risk profiles specific to each of the metric risk profilers 231-235. The metric risk profiles may incorporate overall study data 60 and/or historic data 70, as will now be explained in more detail.

Figure 3A:
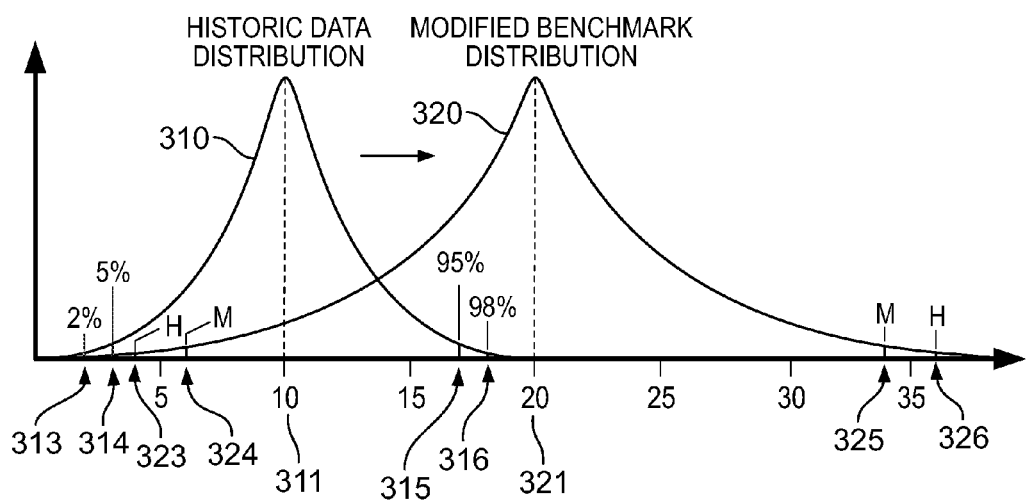
FIGS. 3A-3C are illustrations of metric risk profiles according to embodiments of the present invention.
Figure 3B:
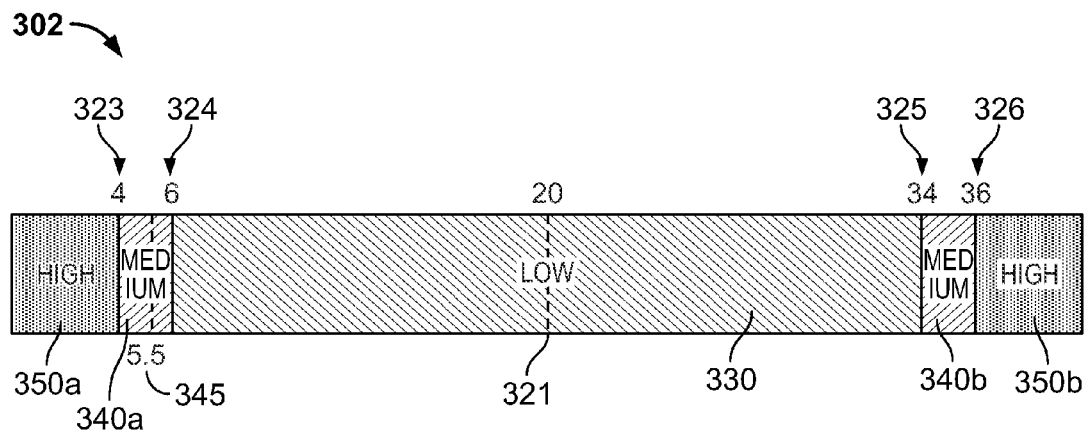
Figure 3C:
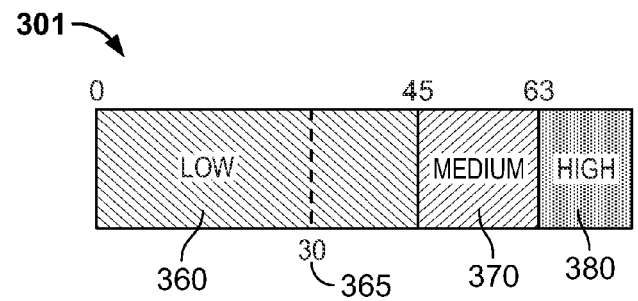

FIGS. 3A-3C are illustrations of metric risk profiles according to embodiments of the present invention. Specifically, the figures illustrate how historic and study data may be used to generate a metric risk profile for a metric. As described further below, each of the metrics discussed above (query rate, subject visit to entry cycle time, etc.) is typically associated with a specific metric risk profile. Historic or industry data 70 may come from studies performed in similar therapeutic areas or with similar numbers or types of sites or from similar clinical trial phases, or a combination of such factors.

FIG. 3A shows a statistically normal distribution 310 of historic data indicating the mean 311 and the 2nd, 5th, 95th, and 98th percentiles 313-316. These percentiles may be viewed as one or more brackets or ranges of values, each of which contains values that are outliers to a mean or average of historic data distribution 310. For example, values for a particular metric historically falling between the 5th and 95th percentiles on distribution 310 may be viewed as being contained in a "low-risk" region of distribution 310. It may also be determined that values for the metric that historically fell outside the 2nd and 98th percentiles indicated a problem that should have been addressed, in which case this region could be called the "high-risk" region. A "medium-risk" region would then have been between the low-risk and high-risk regions.

More specifically, if the historic mean 311 has a value of 10, historic 2nd, 5th, 95th, and 98th percentiles 313-316 may correspond to data with values 2, 3, 17, and 18. From the collection of study data, it may be determined that the study mean 321 is 20, i.e., twice the value of historic mean 311. This ratio may then be used to modify the historic distribution 310 to generate modified benchmark distribution 320. Risk-indicator threshold values (the points bounding the risk regions) for the study would be calculated using the same ratio, 2 in this example, of the study mean to the historic mean. In this example, the values in the historic data distribution 310 corresponding to risk-indicator thresholds 323-326 for modified benchmark distribution 320 would be increased by the factor of 2 to 4, 6, 34, and 36, respectively. Thus, values 4 and 36 would be the high-risk-indicator thresholds 323 and 326 (indicated by "H"), and values 6 and 34 would be the medium-risk-indicator thresholds 324 and 325 (indicated by "M"). Values between risk-indicator thresholds 324 and 325 would correspond to a low-risk region on the modified benchmark distribution 320.

FIG. 3B shows another view of modified benchmark distribution 320 as a double-sided metric risk profile 302. As in FIG. 3A, the value of study mean 321 is 20, and values 4 and 36 correspond to high-risk-indicator thresholds 323 and 326, and values 6 and 34 correspond to medium-risk-indicator thresholds 324 and 325. Low-risk region 330 lies between risk-indicator thresholds 324 and 325; medium-risk regions 340a and 340b lie between risk-indicator thresholds 323, 324 and 325, 326, respectively, and high-risk regions 350a and 350b lie outside of risk-indicator thresholds 323 and 326, respectively.

Some metrics may use single-sided metric risk profiles, e.g., having a minimum and only one or more risk-indicator thresholds outside that minimum. The single-sided metric risk profile may be considered a special case of the double-sided metric risk profile. FIG. 3C shows single-sided metric risk profile 301 which may have 0 as a minimum. Thus, a low-risk region 360 may lie below, for example, the value 45 of the metric, a medium-risk region 370 may lie between values of 45 and 63, and a high-risk region 380 may have a value of greater than 63.

As with double-sided metric risk profiles, the risk-indicator thresholds corresponding to the values 45 and 63 may be determined by modifying specific historic-distribution percentiles, as was shown in FIG. 3A. For example, the historic mean may be 20, with 95th and 98th percentiles corresponding to values 40 and 56. If the study mean is 22.5, then the ratio of study mean to historic mean is 1.125, the value corresponding to the medium-risk-indicator threshold can be calculated as 40*1.125=45, and the value corresponding to the high-risk-indicator threshold can be calculated as 56*1.125=63.

Generally, the metric risk profiles shown in FIGS. 3A-3C comprise a benchmark and risk regions that can be determined in relation to deviations from the benchmark. (In this context, a region of no risk may be considered a "risk region.") The benchmark may be a historic mean or median, an industry mean or median, a study mean or median, or combinations of these. The benchmark could also be a minimum (such as 0) or a maximum. Deviations from the benchmark may be determined based upon percentiles (e.g., 2nd, 5th, 95th, 98th) within a statistical distribution, standard deviations, portions of standard deviations (e.g., one-half of a standard deviation, 3.5 standard deviations), percent deviations from the benchmark (e.g., 5% and 10% deviation), fractions of a range, or other values of statistical significance. Moreover, the risk-indicator thresholds do not need to be symmetric around the benchmark nor be part of a statistically normal distribution.

FIGS. 3A-3C show three risk indicator regions, but there could be more or fewer risk indicator designations depending on the granularity desired by the user (e.g., the sponsor or CRO) or the risk assessment apparatus designer. For example, a system or method employing two risk indicator designations will be appreciated as accomplishing the advantages of the present invention, as will a system or method employing a very large number of risk indicator designations.

Once metric risk profile 301 or 302 is generated, the site-metric risk indicators can be determined. In FIG. 3B, the value 345 for the metric for the site is 5.5. Since this value falls within medium-risk region 340a, the corresponding site-metric risk indicator for that metric at that site is determined to be "medium," or other designation, and this site-metric risk indicator can then be utilized in generating a site-level quality score, e.g., 281. In FIG. 3C, the value 365 for the metric for the site is 30. Since this value falls within low-risk region 360, the risk indicator for that metric at that site may be considered to be "low," or other designation, and this site-metric risk indicator can likewise be used to generate the site-level quality score. In addition to determining site-metric risk indicators for individual sites, embodiments of the present invention can determine the risk indicator for groups of sites, such as, for example, a city, region, state, country, continent, or study as a whole, or other groupings of sites not related to geography.

Referring to FIG. 2B, after all of the metrics for a site (e.g., site 112) have been grouped, normalized, or aggregated into site-metric risk indicators (e.g., R1-R5), an aggregator such as aggregator 241 aggregates site-metric risk indicators R1-R5 into a site-level quality score 281 using an aggregation algorithm such as aggregation algorithm 2401. It is desirable that all the site-metric risk indicators that are aggregated to calculate a site-level quality score be determined using the same number of risk regions, e.g., R1-R5 all have L, M, or H designations, so that the aggregation may be performed using comparable metrics.

Various aggregation algorithms may be used. One aggregation algorithm could be:

$$\text{Site-level quality score} = 100 * \left( \frac{L + 0.5M}{L + M + H} \right) \quad (1)$$

where L, M, and H are the quantity of metric values, corresponding to one site of a study, having low, medium, or high designations, respectively. Using equation (1), site-level quality score 281 may range from 0 to 100. Equation 1 may be generalized to yield equation 2:

$$\text{Site-level quality score} = 100 * \left( \frac{aL + bM + cH}{L + M + H} \right) \quad (2)$$

where a, b, and c are coefficients between 0 and 1 that weight the effects of the three different risk indicator designations. Note that Equation 1=Equation 2 when a=1, b=0.5, and c=0. Equation 2 may be further generalized to yield equation 3:

$$\text{Site-level quality score} = K * \left( \frac{aL + bM + cH}{L + M + H} \right) \quad (3)$$

where a, b, and c are coefficients that weight the effects of the three different risk designations and the value K determines the range of the score.

Once site-level quality score 281 is determined, site-level risk indicator 291 may then be determined using site risk profiler 251. Site risk profiler 251 may operate analogously to metric risk profilers 231-235 described above by operation on site-level quality scores rather than site-level metric values, with or without the use of historic data. One site risk profile that may be used is a single-sided profile in which low risk is indicated for a site-level quality score of 95 or above (i.e., between 95 and 100), medium risk is indicated for a site-level quality score of 85 to 95, and high risk is indicated for a site-level quality score below 85 (i.e., between 0 and 85). Of course, there could be more or fewer than three site-level risk designations, and the risk-indicator thresholds need not be 85 and 95, but may be any numbers within the range of the site-level quality score (e.g., between 0 and 100 or, more generally, between the minimum and the maximum "K" in Equation (3)). The choices of quantity of risk designations and risk-indicator thresholds may depend on the desired granularity of the risk analysis, and on the tolerance for possible risk. Moreover, as with the metric risk profiles described above, the site risk profiles may be modified based on actual study data, such that risk-indicator thresholds may change to convey the needed information regarding the actual site and/or study risk.

Table 1 provides examples of possible values of site-level quality scores (SLQS) and site-level risk indicators (SLRI) for a group of five metrics Metric1 through Metric5 and a site risk profile having risk-indicator thresholds of 85 and 95. The site-level quality scores are calculated using Equation 1. Note that in some cases, there may not be enough data for specific measures to determine a metric value or site-metric risk indicator. This results in fewer than five metric values being used to calculate the site-level quality score.

TABLE 1

Site-Level Quality Scores and Risk Indicators
for Possible Combinations of Five Metrics

| #L | 5 | 4 | 4 | 3 | 1 | 1 | 1 |
|---|---|---|---|---|---|---|---|
| #M | 0 | 1 | 0 | 1 | 2 | 2 | 3 |
| #H | 0 | 0 | 1 | 0 | 1 | 2 | 1 |
| SLQS | 100.00 | 90.00 | 80.00 | 87.50 | 50.00 | 40.00 | 50.00 |
| SLRI | Low | Medium | High | Medium | High | High | High |

Table 1 also shows that site-level quality scores need not be unique.

In addition to showing how site-level quality score 281 and site-level risk indicator 291 for site 112 may be generated, FIG. 2B shows similar details for generating site-level quality score 286 and site-level risk indicator 296 for site 126. In that instance, site 126 data may be separated out from study data 60 using site data filter 210, and then site metric processor 226 may separate out the data for Metric1 through Metric5 for site 126 and then calculate M1 126, M2 126, etc., which are the values for Metric1 through Metric5 for site 126. The metric values are then available to metric risk profilers 231-235 to normalize the metrics into a site-metric risk indicator (e.g., low, medium, or high) R26-R30. Aggregator 246 then aggregates the site 126 metric risk indicators R26-R30 into site-level quality score 286 using aggregation algorithm 2406, which may be the same as or different from aggregation algorithm 2401. Once site-level quality score 286 is determined, site-level risk indicator 296 may be determined using site risk profiler 256, which may be the same as or different from site risk profiler 251. Site-level quality scores and site-level risk indicators for the other sites 114, 116, 122, 124 can be determined in the same way as that shown for sites 112 and 126 (not shown in detail in FIG. 2B).

FIG. 2C shows how quality scores and risk indicators may be determined across multiple sites for a given specific metric. The values of the metric, in this example Metric1 (M1), M1 112, M1 114, etc., from the sites are input to metric risk profiler 231. Site-level metric risk indicators R1, R6, R11, R16, R21, R26 (e.g., low, medium, high) may be determined based upon the each site's Metric1 value, e.g., M1 112, M1 114, M1 116, . . . , M1 126. The resulting site-metric risk indicators are then aggregated in aggregator 248 using aggregation algorithm 2408. Aggregation algorithm 2408 may be the same as or different from aggregation algorithms 2401-2406. Aggregator 248 then generates quality score 288 for the multiple sites (i.e., for the group of six sites) for Metric1. A risk indicator 298 for the multiple sites for Metric1 may then be determined using risk profiler 258, which may have a risk profile similar to or different from site risk profilers 251-256.

As an example of FIG. 2C, assume a study is being conducted at seventeen sites, each site having information for Metric1, and the aggregation algorithm 2408 is the same as Equation 1 above. If fifteen of the sites have a low risk indicator (L), one site has a medium risk indicator (M), and one site has a high risk indicator (H), the quality score for Metric1 for the seventeen sites =

$$100 * \left( \frac{L + 0.5M}{L + M + H} \right) = 100 * (15 + 0.5 * (1))/17 = 91.18.$$

If the risk profile utilized in risk profiler 258 is the same as that used in site risk profiler 251 in the above example, where risk-indicator thresholds are at 85 and 95, then risk indicator 298 for the seventeen sites will be designated medium, as it is between 85 and 95.

FIG. 2D shows how overall quality scores 289 and overall risk levels 299 may be determined for multiple sites AND for multiple metrics, for example, in order to determine such values at a country level or study level. The metric values M1 112 to M1 126, M2 112 to M2 126, etc., from each of the sites being aggregated are made available to their respective metric risk profilers. In more detail, the values for Metric1 from each of the sites are input to metric risk profiler 231, the Metric2 values from the sites are input to metric risk profiler 232, etc. for the Metric3, Metric4, and Metric5 values. For five metrics and six sites, thirty site-metric risk indicators R1-R30 may be generated (unless there is insufficient data for a specific metric at a site). The thirty risk indicators may then be aggregated in aggregator 249 using aggregation algorithm 2409, which may be the same as or different from aggregation algorithms 2401-2406 and 2408. Aggregator 249 then generates an overall quality score 289 for the corresponding multiple sites and multiple metrics. An overall risk level 299 for the multiple sites and multiple metrics may then be determined using risk profiler 259, which may have a risk profile similar to or different from site risk profilers 251-256 and 258.

As an example of FIG. 2D, assume again that there are seventeen sites for country 1, with each site having five metrics Metric1-Metric5, and the aggregation algorithm 2409 is the same as Equation 1 above. Below is a table of the data:

TABLE 2

Country-Level Quality Scores for Five Metrics

|  | Overall | Metric1 | Metric2 | Metric3 | Metric4 | Metric5 |
|---|---|---|---|---|---|---|
| #L | 76 | 16 | 13 | 15 | 17 | 15 |
| #M | 6 | 1 | 2 | 1 | 0 | 2 |
| #H | 3 | 0 | 2 | 1 | 0 | 0 |
| Quality Score | 92.94[2] | 97.06[1] | 82.35[1] | 91.18[1] | 100.00[1] | 94.12[1] |

TABLE 2-continued

Country-Level Quality Scores for Five Metrics

|  | Overall | Metric1 | Metric2 | Metric3 | Metric4 | Metric5 |
|---|---|---|---|---|---|---|
| Risk Indicator | Medium | Low | High | Medium | Low | Medium |

[1]Quality score derived using aggregation algorithm 2408.
[2]Quality score derived using aggregation algorithm 2409.

Table 2 shows eighty-five site-metric risk indicators in total (17*5). (There may be fewer than eighty-five site-metric risk indicators if there were insufficient data for some metrics at some sites.) Each of the metrics can have a score calculated according to FIG. 2C, but all eighty five site-metric risk indicators are aggregated to calculate the overall quality score of 92.94 for the country. Where the overall quality score is between 85 and 95, the overall risk indicator for that country will be medium.

A study-level score and risk indicator can be generated in much the same way, where all of the metric values for all of the sites are used.

Instead of aggregating all site-metric risk indicators for all sites in a study to generate an overall quality score at the country or study levels, a different aggregation could be performed. Taking the country-level example above, with seventeen sites each having five metrics, instead of aggregating the eighty-five site-metric risk indicators, the five metric risk indicators across the seventeen sites could be aggregated, where each metric risk indicator is generated according to FIG. 2C. Alternatively, risk indicators could be generated for each site for all five metrics, such as is done to generate site-level risk indicators 291-296 in FIG. 2B, and then those risk indicators could be aggregated across the seventeen sites to generate an overall quality score and/or risk indicator.

The parts and blocks shown in FIGS. 1 and 2A-2D are examples of parts that may comprise system 100 and risk assessment apparatus 10, and do not limit the parts or modules that may be included in or connected to or associated with system 100 and risk assessment apparatus 10. For example, as mentioned before, site data filter 210 and site metric processors 221-226 may not be used if the specific data outputs of those blocks are available to risk assessment apparatus 10 in another manner, such as being directly communicated from the sites or directly presented to risk assessment apparatus 10 via a medium such as a CD, DVD, or thumb or flash drive. In other embodiments, site data filter 210 and site metric processors 221-226 may reside in different physical "boxes" or devices, and the connections between them may be wired or wireless, via physically close connections or over a network, in a manner similar to connection 35. Moreover, although metric risk profilers 231-235 are shown as separate blocks, they may be part of the same hardware or software routine but just have different input variables that determine the metric risk profiles themselves. Similarly, although site metric processors 221-226 are shown as separate blocks, they may be part of the same hardware or software routine but just have different processing rules that determine how to process the incoming site data to determine the requisite metric values.

Figure 4A:
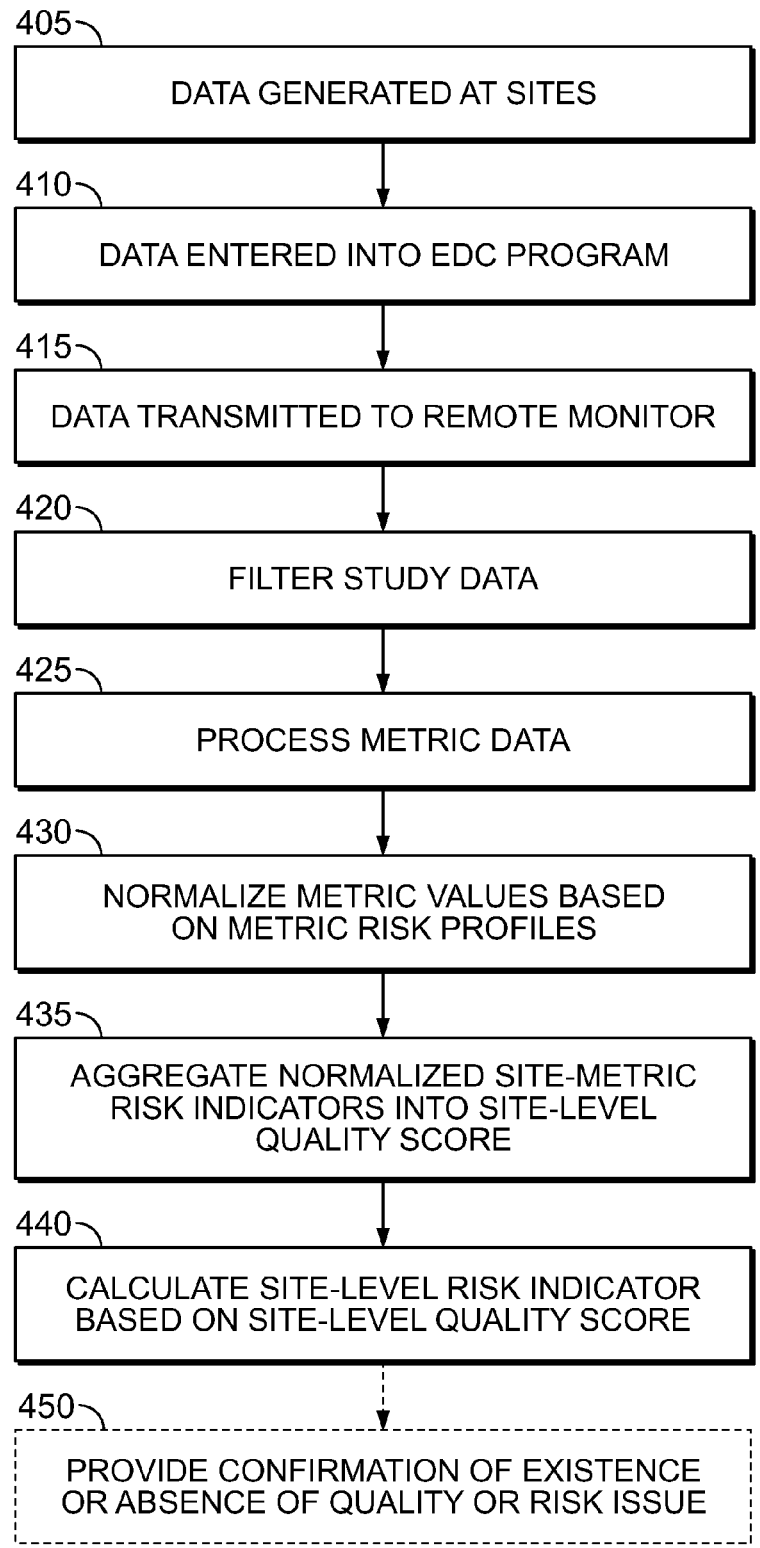
FIGS. 4A-4C are flowcharts illustrating the general operation of a risk assessment apparatus according to an embodiment of the present invention.
Figure 4B:
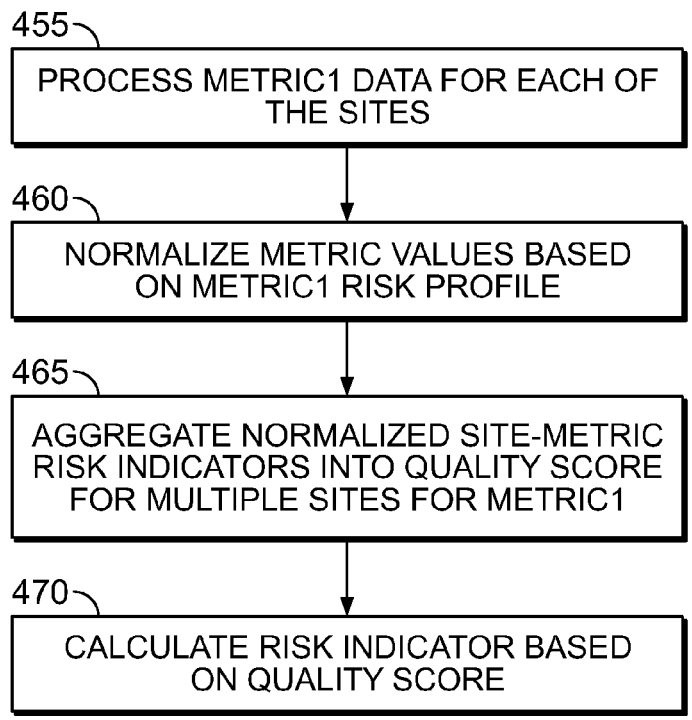
Figure 4C:
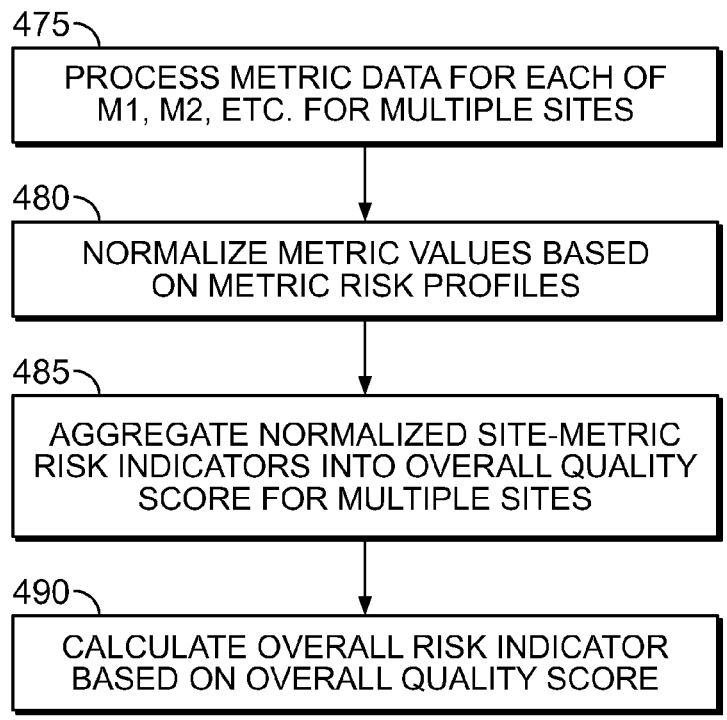

Reference is now made to FIGS. 4A-4C, which are flowcharts illustrating the general operation of a system that includes risk assessment apparatus 10 according to an embodiment of the present invention. In FIG. 4A, data may be generated at the various sites (operation 405). In operation 410, the data may be entered into an electronic data capture (EDC) program at the various sites. In operation 415, the data may be transmitted from the sites to a remote or central monitoring apparatus, such as risk assessment apparatus 10. In operation 420, risk assessment apparatus 10 may filter each site's data from the study data and then, in operation 425, process the metric data for the sites to determine metric values. In operation 430, the metric values may be normalized based on metric risk profiles. Typically, each metric value will be normalized by a specific metric risk profile, but it is also possible that the same metric risk profile will be used to normalize more than one metric value. In operation 435, the normalized site-metric risk indicators may be aggregated into a site-level quality score for each site according to an aggregation algorithm. In operation 440, the site-level quality score may be used to generate a site-level risk indicator. Operation 450, which will be described further below in connection with another embodiment of the present invention, could provide confirmation of the existence or absence of an actual quality or risk issue by a site monitor visit to the site or by an action or step taken at the site itself.

The flowcharts in FIGS. 4B and 4C illustrate how higher-level quality scores can be generated based on the site-level metric risk indicators calculated in operation 430. "Higher-level" in this case refers to groupings or geographies that are more inclusive than site level, e.g., regional level, state level, country level, study level, etc. Groupings by geographic region are illustrative, but any relevant groupings having a common element may apply. For example, higher-level site quality scores may be generated for groups of sites managed by each CRA in the study. FIG. 4B illustrates the process generally associated with FIG. 2C in which a quality score and risk indicator can be calculated for a specific metric, e.g., Metric1, from a plurality of sites. In operation 455, the data for Metric1 are processed for each of the sites to determine metric values. In operation 460, the metric values may be normalized based on the Metric1 risk profile into site-metric risk indicators. In operation 465, the site-metric risk indicators may be combined or aggregated into a quality score for the multiple sites. In operation 470, a risk indicator for the multiple sites for Metric1 may be calculated from the quality score.

FIG. 4C illustrates the process generally associated with FIG. 2D in which a quality score and risk indicator can be calculated for a number of metrics, e.g., Metric1, Metric2, . . . , Metric5, from a plurality of sites. In operation 475, the data for the metrics may be processed for each of the sites to determine metric values. In operation 480, the metrics may be normalized into site-metric risk indicators based on the specific metric risk profiles. In operation 485, the site-metric risk indicators may be combined or aggregated into an overall quality score for the multiple sites and metrics. In operation 490, an overall risk indicator for the multiple sites and metrics may be calculated from the overall quality score.

Besides the operations shown in FIGS. 4A-4C, other operations or series of operations may be used to calculate quality scores and risk indicators. Moreover, the actual order of the operations in the flowchart may not be critical.

Figure 5:
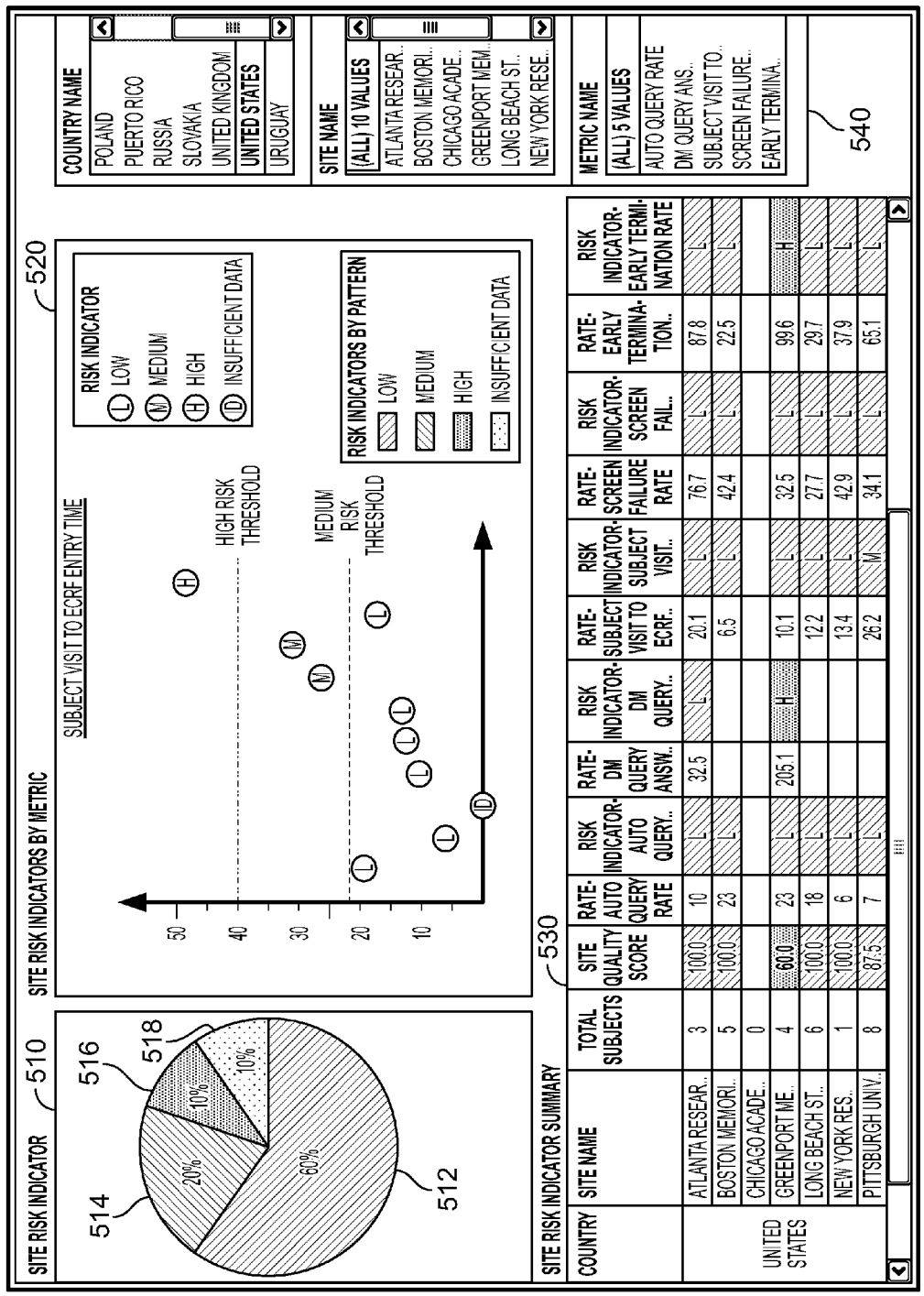
FIG. 5 is an illustration of a graphical interface for displaying site-level data according to an embodiment of the present invention.

Risk assessment apparatus 10 may have a graphical interface for displaying study and site data and risk indicators. FIG. 5 shows an example of a site-level view of quality data scores and risk indicators for ten sites in one study. In the embodiment illustrated in FIG. 5, the interface may include four main parts, 510, 520, 530, and 540. Part 510 is a pie chart showing at a glance the percentage of sites falling within each risk indicator designation (512, 514, 516) or having insufficient data (518) for the overall quality score. Part 520 may show the values for a certain metric, in this case, Subject Visit to eCRF Entry Time, for each site, and may also show the risk-indicator thresholds for that metric. In this example, values less than 22 are low risk, values between 22 and 40 are medium risk, and values above 40 are high risk. Part 530 may show the values and quality scores numerically for each of the five metrics for each of the sites in the study, as well as the site-level quality score for each site ("Site Quality Score"), which is a combination of the metric risk indicators for the five metrics for that study. Part 530 may also pattern or color code according to risk indicator the metric risk indicators and the Site Quality Score. Part 530 may also include information regarding the number of subjects within each site. Part 540 may be a filter area, by which the user may select data that satisfy specific criteria, such as country, site name, and metric name, and the information shown in parts 510, 520, and 530 could change based on those filters.

In the example shown in FIG. 5, the United States is chosen as the filter country, and there are ten sites within the United States. In Part 510, six of the ten sites (60%) are low-risk, two are medium-risk, one is high-risk, and one does not have sufficient data to be evaluated. Part 530 shows the values of five metrics, auto-query rate, data management (DM) query answer wait time, subject visit to eCRF entry time, screen failure rate, and early termination rate, along with the metric risk indicators for those metrics and the site-level quality scores for the sites (although data for only seven sites are actually shown). Part 520 shows the values of one of the metrics, subject visit to eCRF entry time, for all ten sites, and includes the risk indicator for each site for that metric.

Figure 6:
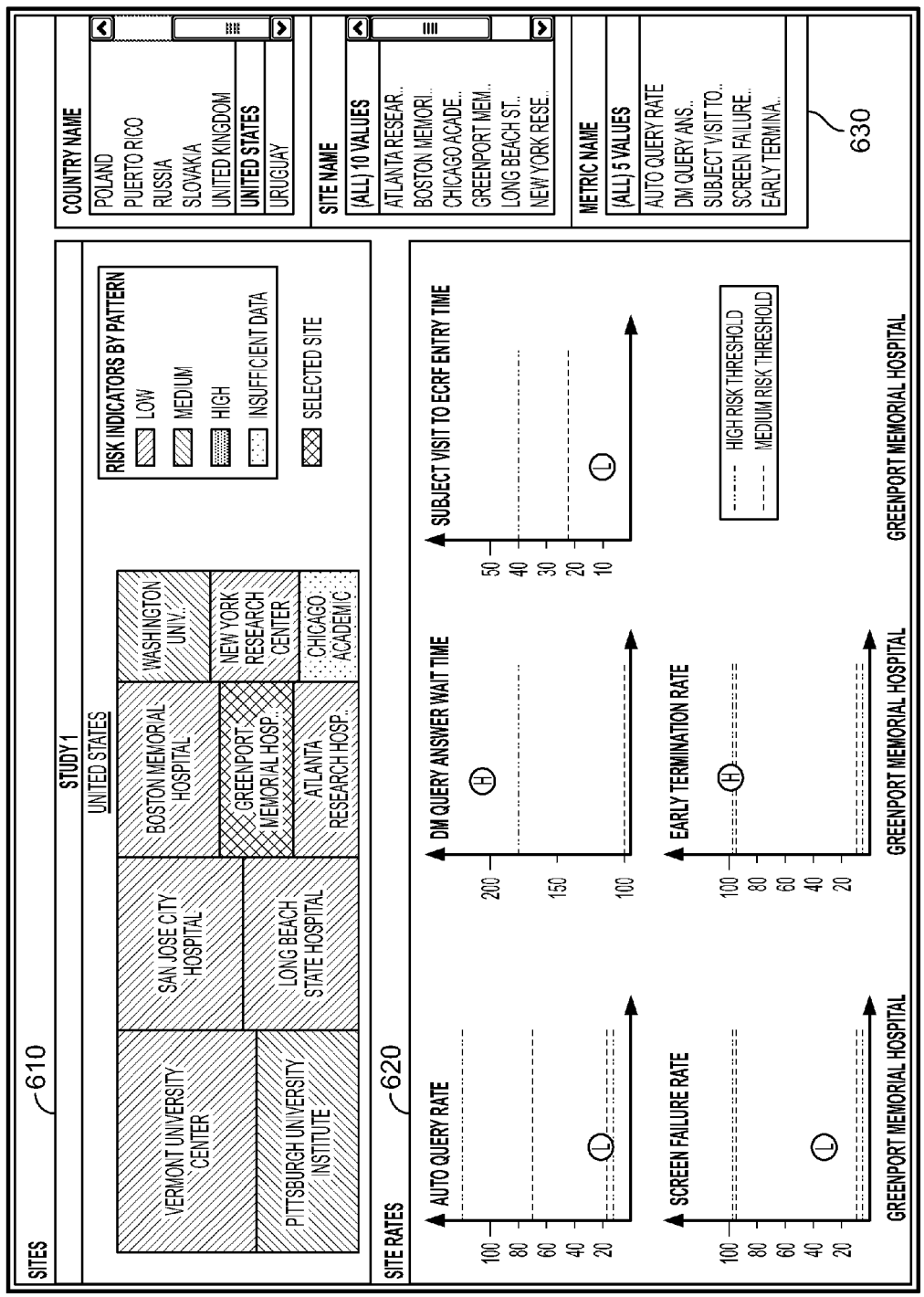
FIG. 6 is an illustration of a graphical interface for displaying another view of site-level data according to an embodiment of the present invention.

FIG. 6 shows another site-level view of quality data scores and risk indicators for the ten sites in FIG. 5. In the embodiment illustrated in FIG. 6, the interface may include three main parts, 610, 620, and 630. Part 610 is a pattern-coded (alternatively, color-coded) chart of all the sites showing at a glance the risk indicator for each site. An additional pattern/color may be used to denote the specific site chosen to view in Part 620, here Greenport Memorial Hospital. The size of the rectangles in Part 610 may indicate size (e.g., number of subjects) of the particular study. Part 620 may show the values of the metrics for the specific site chosen in Part 610, and into which risk regions those values fall. Part 620 may also show the risk-indicator thresholds for each metric. Part 630 may be a filter area, by which the user may select data that satisfy specific criteria, such as country, site name, and metric name, and the information shown in parts 610 and 620 could change based on those filters.

The example shown in FIG. 6 continues the one shown in FIG. 5, so the United States is chosen as the filter country and all ten of the sites within the United States are displayed in Part 610. Greenport Memorial Hospital is selected in Part 610 as shown by the different pattern for that site. The values of the five metrics, auto-query rate, data management (DM) query answer wait time, subject visit to eCRF entry time, screen failure rate, and early termination rate, are displayed in Part 620, along with the risk-indicator thresholds for those metrics for that site. Auto-query rate, screen failure rate, and early termination rate have double-sided metric risk profiles, such as metric risk profile 302 shown in FIG. 3B, in which there are medium-risk-indicator thresholds and high-risk-indicator thresholds both above and below the metric benchmark (which is not specifically shown in FIG. 6). In the example in FIG. 6, the value of auto-query rate is 23, which is low risk, the two medium-risk-indicator thresholds are 70 and 18, and the two high-risk-indicator thresholds are 120 and 12. As before, other embodiments of the invention may have more or less than three risk indicator designations and the risk-indicator thresholds may differ from these values, depending on the study, user (e.g., the sponsor or CRO), or risk assessment apparatus designer.

Figure 7:
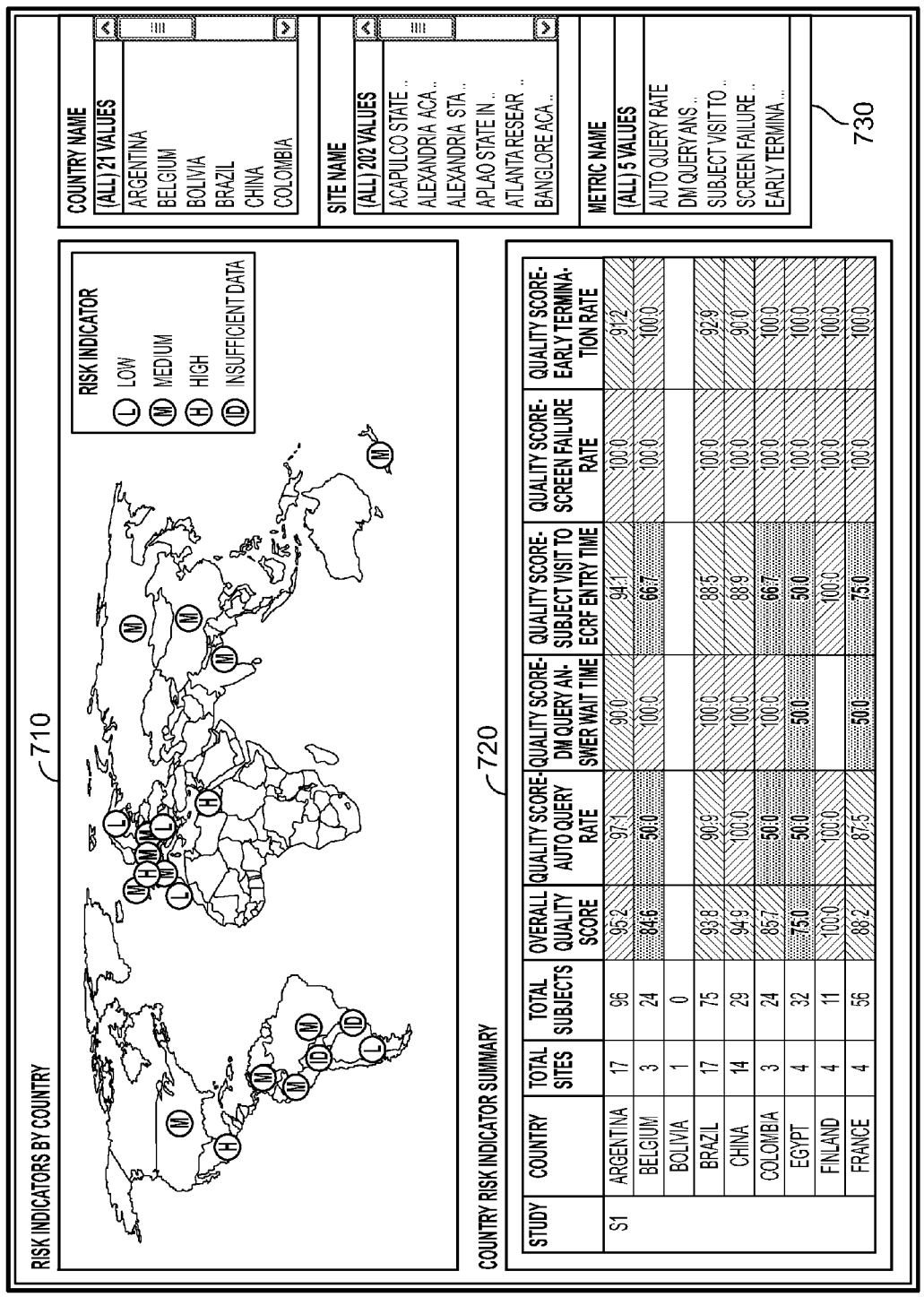
FIG. 7 is an illustration of a graphical interface for displaying country-level data according to an embodiment of the present invention.

FIG. 7 shows a country-level view of quality scores and risk indicators for one study. In the embodiment illustrated in FIG. 7, the interface may include three main parts, 710, 720, and 730. Part 710 may include a world map, which may show at a glance country-level risk based on pattern or letter or color coding. Part 720 may show the quality scores numerically for each of five metrics for each of the countries in the study, each of which is an aggregation of the site-metric risk indicators as illustrated in FIG. 2C. Part 720 may also show the overall quality score for each country, which is an aggregation of the site-metric risk indictors for that study, as illustrated in FIG. 2D. Part 720 may also pattern or color code according to risk indicator the metric quality scores and the overall quality score. Part 720 may also include information regarding the number of sites for each country. Part 730 may be a filter area, by which the user may select data that satisfy specific criteria, such as country, site name, and metric name, and the information shown in parts 710 and 720 could change based on those filters.

In the example shown in FIG. 7, a metric quality score or an overall quality score of 85 or less generates a high risk indicator, a score between 85 and 95 generates a medium risk indicator, and a score above 95 generates a low risk indicator. As before, other embodiments of the invention may have more or less than three risk indicator designations and the risk-indicator thresholds may differ from 85 and 95, depending on the study, user (e.g., the sponsor or CRO), or risk assessment apparatus designer.

Figure 8:
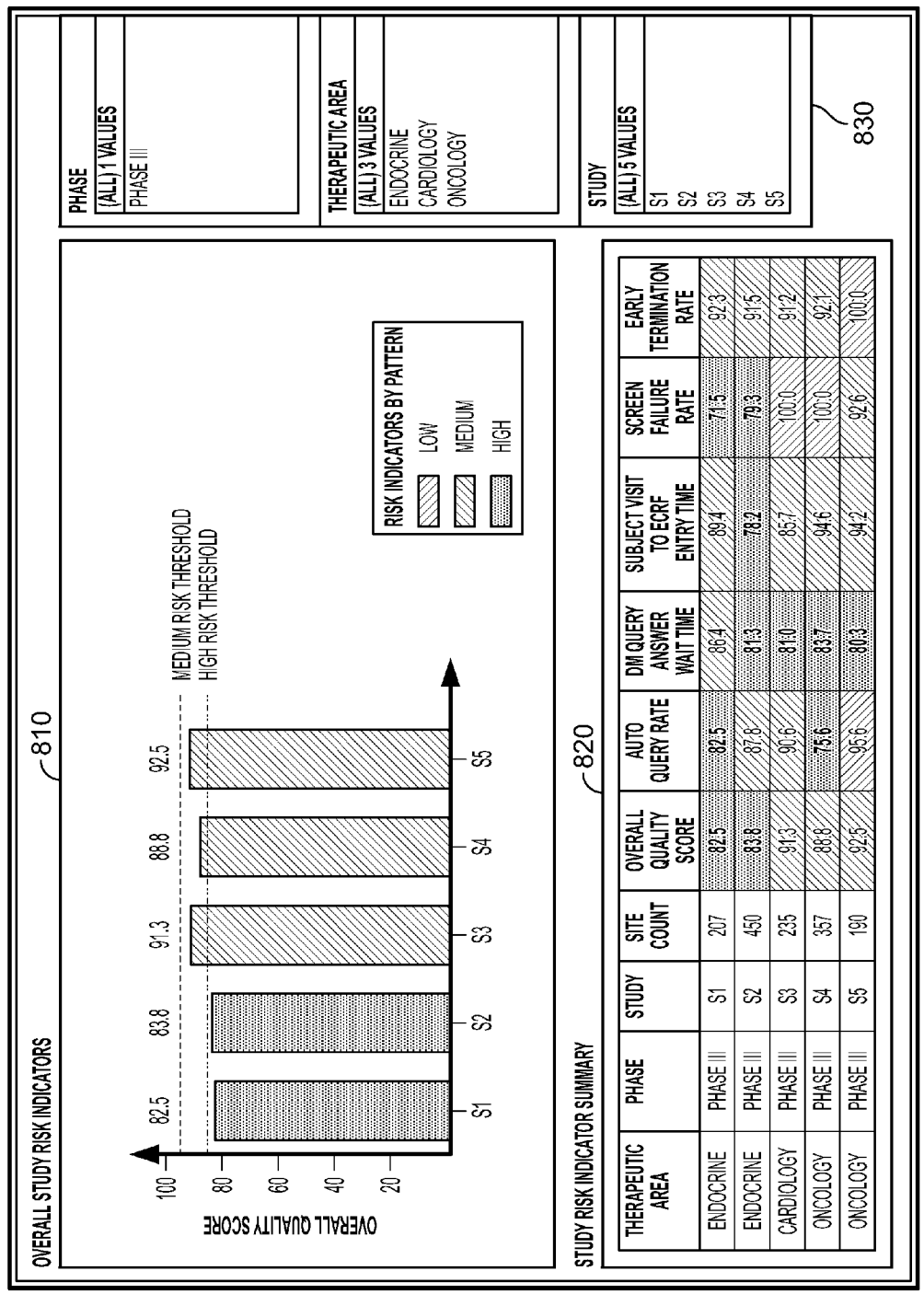
FIG. 8 is an illustration of a graphical interface for displaying overall study data according to an embodiment of the present invention.

FIG. 8 shows an "executive" or overall view of quality scores and risk indicators for several studies. In the embodiment illustrated in FIG. 8, the interface may include three main parts, 810, 820, and 830. Part 810 may include a bar graph, in which the overall study-level quality score is shown relative to risk-indicator thresholds, and the bars of the graph may be pattern or color coded according to risk indicator. Part 820 may show the quality scores numerically for each of five metrics for five studies S1 through S5, which may be derived as illustrated in FIG. 2C, as well as the overall quality score for each study, which may be an aggregation of the site-metric risk indicators for that study, which may be derived as illustrated in FIG. 2D. Part 820 may also pattern or color code according to risk indicator the metric quality scores and the overall quality scores. Part 820 may also include information regarding the number of sites for each study, in which clinical trial phase the study was performed, and in which therapeutic area the study was classified. Part 830 is a filter area, by which the user may select studies that satisfy specific criteria, such as clinical trial phase, therapeutic area, or drug/study name, and the information shown in parts 810 and 820 could change based on those filters.

In the example shown in FIG. 8, an overall study quality score of 85 or less generates a high risk indicator, a score between 85 and 95 generates a medium risk indicator, and a score above 95 generates a low risk indicator. As before, other embodiments of the invention may have more or less than three risk indicator designations and the risk-indicator thresholds may differ from 85 and 95, depending on the study, user (e.g., the sponsor or CRO), or risk assessment apparatus designer.

Reference is now made to describing examples of site quality metrics in more detail. These include auto-query rate, data management (DM) query answer wait time, subject visit to electronic case report form (eCRF) entry time, screen failure rate, and early termination rate.

Clinical data entered into an EDC system by clinicians, study coordinators, or other site personnel may be remotely analyzed in order to identify issues with the quality of that data and, in turn, with the quality of the site conducting the clinical trial. In addition, metadata generated in conjunction with clinical data entered into the EDC system, on its own or in relationship to the clinical data, may also be useful in identifying issues with the quality of the site conducting the clinical trial. Examples of the usefulness of harnessing clinical data and/or its associated metadata will be apparent in the following inventive examples of site quality metrics.

Auto-Query Rate.

In a clinical trial, a "query" may be generated in a number of ways, such as to catch a data entry error made by clinical site personnel or to question the value or validity of datapoints (a "datapoint" is typically any data entry opportunity) based on either their value only or their value relative to other entered data points (which may or may not be true errors). As discussed herein, EDC programs may recognize such entries and may automatically log such queries and prompt the site personnel to correct the entry. For example, if a subject's age is to be entered, a query may be configured to be generated automatically if the age entered is too young or too old or not a number.

Because the data subject to query generation by an EDC program may be programmed by the user (e.g., the sponsor or CRO) or by the EDC vendor, the types of queries generated may vary from study to study. Moreover, not every datapoint nor every data entry error generates a query. In any case, the EDC program may be configured to track the number of automatic queries that are generated during data entry and may determine the rate of these automatically generated queries (or "auto-queries"). Embodiments of the present invention may identify and solve data quality issues based on a meaningful auto-query rate, i.e., an auto-query rate that is generated after a minimum number of datapoints is collected, for example 300. In other words, for the auto-query rate for a given site to be meaningfully compared to that of another site, it may be desirable that the auto-query rate for those sites exceed a minimum quantity of datapoints. In addition, newer data may generally be considered on a rolling basis (e.g., the last 1000 datapoints) so as to allow for a more sensitive identification of emerging issues. Otherwise, a recent change in the auto-query rate could be more difficult to identify if it were combined with all of the data for the site.

In one embodiment of the present invention, the auto-query rate may be subject to a double-sided metric risk profile, similar to profile 302 shown in FIG. 3B. The benchmark chosen may be historic, in which case it may be based on historic data for clinical trials in a specific therapeutic area or clinical trial phase or based on other data preceding the current study. One benchmark often chosen may be the historic mean, which is typically the 50th percentile (if the distribution of auto-queries is statistically normal). A historic data distribution may be set up that includes the 2nd, 5th, 95th, and 98th percentiles, as described in FIG. 3A. The benchmark could be modified to be the study mean, and the risk-indicator thresholds for the modified distribution would be the values for the historical 2nd, 5th, 95th, and 98th percentiles multiplied by the ratio of the study mean to the historic mean, as described with respect to FIGS. 3A-3C.

If there are three risk indicator designations, low, medium, and high, associated with auto-query rate, in one embodiment of the present invention the low-risk region may be between the modified 5th and 95th percentiles, the medium-risk region may be between the modified 2nd and 5th percentiles on the low end and the modified 95th and 98th percentiles on the high end, and the high-risk region may be below the modified 2nd percentile on the low end and above the modified 98th percentile on the high end.

A site-level metric for auto-query rate may be calculated as follows: since this may be a rolling metric, divide the number of auto-queries generated from the last 1000 datapoints from each of the subjects at the site. If there are 10 subjects and 500 auto-queries in this period, then the auto-query rate=500/10,000=5%. This number would be compared to the modified 2nd, 5th, 95th and 98th percentile values in the modified distribution to determine the appropriate risk indicator for auto-query rate for the given site. (Note that in this example, the 5% auto-query rate is not the same as the 5th percentile of the data distribution.)

DM Query Answer Wait Time.

In typical clinical trials, certain personnel known as data managers may review data entered into the EDC program. If a data manager identifies an issue such as an inconsistency or deficiency with entered data, he or she may manually enter a query into the EDC program concerning the entered data. The EDC program may flag those manual queries for site personnel to respond to. The EDC program can track the mean time taken by site personnel to respond to the data manager's query.

In one embodiment of the present invention, the DM query answer wait time may be subject to a single-sided metric risk profile, similar to profile 301 shown in FIG. 3C. As with auto-query rate, the benchmark chosen for DM query answer wait time may be historic, e.g., the historic mean, and the benchmark and metric risk profile may be modified by current study data. As with auto-query rate, low, medium, and high risk indicator designations may be chosen, with the same or different percentile assignments. The actual calculation for this metric may comprise the mean DM query answer wait time.

In one embodiment, mean DM query answer wait time may be calculated only for queries that have actually been answered and for unanswered queries that have been pending more than a certain number of days, e.g., 15 (so as to not skew results caused by pending queries of short duration). In the latter case, the DM query answer wait time can be set at the number of days pending until the query is answered, at which time it assumes its actual value. In order to have a meaningful metric, a minimum of 10 answered queries may be imposed, as well as looking at only the 20 most recently answered queries, so as to identify emerging issues, as was mentioned with respect to auto-query rate. (The choices of 15 pending days, 10 minimum answered queries, and the 20 most recently answered queries are examples only; they may be changed to lower or higher numbers.) As an example of this metric, if the distribution of the 20 most recently answered query wait times is 3 of 4 days, 4 of 6 days, 8 of 7 days, 2 of 8 days, and 3 that have not yet been answered but have been pending for 18 days, the mean DM query answer wait time is (3*4+4*6+8*7+2*8+3*18)/20=8.1 days.

A study-level metric for DM query answer wait time may be calculated as follows: find the median of the site-level metrics for DM query answer wait time. "Median" may be chosen for study-level data rather than "mean," which may be chosen for site-level data, because extreme outlier values (e.g., >150 days) may have a greater impact on the study-level metric if the mean were taken rather than the median. Outliers at a particular site, however, should be identified, but they might be masked were the median used at the site level rather than the mean.

Subject Visit to eCRF Entry Time.

Similar to the site quality metric DM query answer wait time, subject visit to eCRF entry time measures the delay from the date of a subject visit to the date that the subject visit is entered into the EDC program, as reflected by the metadata timestamp recorded when the subject visit date is entered. A mean value may be determined for every site that has sufficient data to calculate a value for this metric.

In one embodiment of the present invention, like the DM query answer wait time, the subject visit to eCRF entry time may also be subject to a single-sided metric risk profile, similar to profile 301 shown in FIG. 3C. As with DM query answer wait time, the benchmark chosen for subject visit to eCRF entry time may be historic, e.g., the historic mean, and the benchmark and metric risk profile may be modified by current study data. As with DM query answer wait time, low, medium, and high risk indicator designations may be chosen, with the same or different percentile assignments. The actual calculation for this metric may comprise the mean subject visit to eCRF entry time.

In one embodiment, in order to have more meaningful data, mean subject visit to eCRF entry time may be calculated only for sites having at least three patient visits, and the 15 most recent visits may be used on a rolling basis. (The choices of three minimum visits and the 15 most recent visits are examples only; they may be changed to lower or higher numbers.) As an example of this metric, if the distribution of the 15 most recent visits is 3 of 4 days, 4 of 6 days, and 8 of 7 days, the mean subject visit to eCRF entry time is (3*4+4*6+8*7)/15=6.13 days.

A study-level metric for subject visit to eCRF entry time may be calculated using the median of the site-level metrics for subject visit to eCRF entry time, just as was done for study-level DM query answer wait time. As before, the median may be chosen for study-level data rather than the mean, because outliers within a site should be noticed (using the mean), but a site outlier in the whole study does not have as much weight, so the median can be used.

Screen Failure Rate.

Screen failure rate reflects the percentage of subjects that were initially determined to be eligible for a study, but were subsequently dropped from the study prior to being randomized. Screening may begin when a subject is first considered for a clinical trial, and is entered into the EDC program. A site may go through weeks of ensuring that a subject remains eligible for a study as determined by the study's inclusion and exclusion criteria. A high screen failure rate can indicate a site quality issue: a site could be taking advantage of the sponsor's paying for procedures and care during screening. A screen failure rate that is too high especially compared to other sites in the study suggests the site may have been screening too broadly, and may not be adhering to the study protocol with regard to identifying patients to screen.

A screen failure rate that is too low may be an indication that those variables that are used to determine eligibility are not being fully and/or accurately identified.

In one embodiment of the present invention, because both high and low screen failure rates may be indicative of lower quality data, this metric may be subject to a double-sided metric risk profile, similar to profile 302 shown in FIG. 3B. As with auto-query rate, low, medium, and high risk indicator designations may be chosen, with the same or different percentile assignments. However, unlike the prior metrics, the benchmark chosen for screen failure rate is not typically historic. Instead, the benchmark may be a site-level "p-score," which is similar to a statistical "p-value." The site-level p-score may represent the probability that a site's screen failure rate would be less than the current site's screen failure rate, assuming that screen failures are expected to occur at the same rate as the current study-level rate. The site-level p-score has a value from 0 to 100, where sites with a screen failure rate equal to the study-level rate will have a p-score value of 50, sites with high screen failure rates will have p-scores approaching 100, and sites with low screen failure rates will have p-scores approaching 0. The site-level p-score may use a normal approximation to a binomial distribution.

A study-level metric for screen failure rate may be calculated as:

$$\frac{0.05 + \text{sum(site total screen failed subjects)}}{0.1 + \text{sum(site total screened subjects)}} \quad (4)$$

As an example, if there is one patient at the site and that one patient drops out, the screen failure rate would be 100%. A second site with 10 patients, all of whom drop out, would also have a 100% screen failure rate. The use of a p-score will assess these sites differently, however, because the p-score considers not just the screen failure rate, but the number of patients that contribute to that rate. In this example, the site with 10 patients would have a more extreme p-score than the site with just 1 patient.

Early Termination Rate:

Early termination rate measures the rate at which subjects have been randomized into a study and have then dropped out before the study has been completed. A low early termination rate may indicate that a site is acting improperly to retain subjects who do not meet the inclusion or exclusion criteria of a study. A high early termination rate may indicate that a site is mismanaging subjects in earlier stages of the study process, for example, by not informing the subjects regarding the study requirements.

Early termination rate may be treated similar to screen failure rate in terms of metric risk profile (double-sided), number of risk indicator designations, and percentile assignments. Early termination rate may also use a site-level p-score rather than historical data for its benchmark. As with screen failure rate, the site-level p-score may use a normal approximation to a binomial distribution.

A study-level metric for screen failure rate may be calculated as follows:

$$\frac{0.05 + \text{sum(site total early terminated subjects)}}{0.1 + \text{sum(site total enrolled subjects)}} \quad (5)$$

Similar to screen failure rate, this metric will be sensitive to both the value of the observed rate for a site and the number of patients that contribute to that rate.

In another embodiment, remote monitoring of various metrics could be combined with on-site monitoring or site-based feedback in order to provide a dynamic measure of how important each metric is and then weight the metrics accordingly. For example, if a metric, a site quality score, or other higher-level quality score falls within a medium or high risk indicator, a correlation between that risk indicator and an actual quality or risk issue at the site could be determined via confirmation of the actual site conditions, such as the existence of a quality or risk issue. Such confirmation could be provided by a site monitor visit to the site or by an action or step taken at the site itself (see operation 450 in FIG. 4A). Operation 450 could also include a confirmation of the absence of an actual quality or risk issue by a site monitor visit to the site or by an action or step taken at the site itself. Such confirmations may provide correlations between risk indicators and the site such that both false positives and false negatives may be identified. In addition, those metrics which gave rise to a medium or high risk indicator may be identified and correlated.

After collecting enough data on correlations between the risk indicator and the existence of increased risk and/or the metrics which gave rise to a medium or high risk indicator, those specific metrics could be weighted in the aggregation algorithm. In the embodiments described earlier, all of the metrics from all of the sites have been weighted the same (except for those for which there is not enough data) in the aggregation algorithm. The aggregation algorithm could be modified as follows: Instead of $$100 * \left( \frac{aL + bM + cH}{L + M + H} \right),$$

the terms in the numerator could change depending on which metric has which risk indicator. For example, if Metric3 is determined to be very important, but Metric1 is determined to be only half as important, then the L, M, and H associated with Metric3 would carry full weight (e.g., $aL_3+bM_3+cH_3$ in the numerator), but the L, M, and H associated with Metric1 would be counted only half as much (e.g., $0.5*(aL_1+bM_1+cH_1)$ in the numerator). This modified aggregation may be rewritten more generally as:

$$100 * \left( \frac{\sum_i m_i(aL + bM + cH)}{\sum_i m_i(L + M + H)} \right) \quad (6)$$

where $m_i$ is the weighting for the $i^{th}$ metric.

Often times those who work with clinical trials need a quick way to judge the quality of a clinical trial site. A score would be one such way to quickly judge the quality of a clinical trial site. Such a score could take far ranging data and countless details and boil that information down in a single score that could be applied to a trial site, a region of trial sites, etc. That score would give an administrator a quick overview of the quality of clinical trials in a brief glance.

The task of monitoring is made even more difficult by the fact that a clinical trial collects thousands of datapoints about the drug being studied and about the hundreds or thousands of clinical trial sites. It is impossible for a site monitor to keep track of all of this data without the intelligent method and apparatus described herein.

In sum, methods and apparatuses are described that may be used to normalize data site metrics and combine a plurality of the metrics to determine a site-level quality score. Normalization may be accomplished by applying metric risk profiles to the metrics. These methods allow clinical trial administrators to review data from multiple clinical trials and clinical trial sites and determine at a glance whether a trial site may be risky or may be providing bad data. Such problem sites can then be addressed as quickly and as efficiently as possible. These methods reduce the cost of monitoring a clinical trial because they focus the monitor's attention on those sites that may not be performing as well as needed. Note that although the methods and apparatuses described herein have been described with respect to clinical trials for drugs, they are applicable to clinical trials for other items such as medical devices, vaccines, and biologics. They are also applicable to systems other than clinical trials that have distributed sites collecting data and for which the integrity of the data and the sites may be monitored.

The techniques described above improve over both total source data verification systems and reduced source data verification systems in which the monitor is still expending energy and time visiting sites that are performing adequately or better.

In contrast to those systems, these techniques provide centralized, remote identification of risk associated with the systems being monitored. In the clinical trial application, these techniques provide the clinical trial sponsor a holistic, quantitative, unbiased profile of each clinical trial site in terms of the quality of the trials being conducted by the site to proactively identify problematic clinical sites.

Aspects of the present invention may be embodied in the form of a system, a method, or a computer program product. Similarly, aspects of the present invention may be embodied as hardware, software or a combination of both. Aspects of the present invention may be embodied as a computer program product saved on one or more computer-readable media in the form of computer-readable program code embodied thereon.

For example, the computer-readable medium may be a computer-readable signal medium or a computer-readable storage medium. A computer-readable storage medium may be, for example, an electronic, optical, magnetic, electromagnetic, infrared, or semiconductor system, apparatus, or device, or any combination thereof.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

Computer program code in embodiments of the present invention may be written in any suitable programming language. The program code may execute on a single computer, or on a plurality of computers. The computer may include a processing unit in communication with a computer-usable medium, wherein the computer-usable medium contains a set of instructions, and wherein the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A computer-implemented method, comprising:
   receiving site data from one or more clinical sites, the site data including clinical monitoring data;
   converting, by a processor, the site data into a site-level data quality score using at least one single-sided or double-sided metric risk profile, wherein:
   the site-level data quality score is based on at least two metrics; and
   the at least one metric risk profile is based on at least clinical study data and historic clinical study data, the clinical study data being received from a plurality of clinical sites and the historic clinical study data having a statistical distribution and a benchmark related to a metric;

calculating a risk indicator based on the site-level data quality score; and generating, by a processor, the at least one metric risk profile in at least substantially real-time by:
- calculating a clinical study benchmark for at least one of the metrics based on the clinical study data;
- automatically scaling the historic clinical study data statistical distribution by a ratio of the clinical study benchmark to the historic clinical study data benchmark; and
- assigning risk regions, utilizing measures of statistical significance, to the scaled statistical distribution; and outputting at least one of said risk indicator and said site-level data quality score.

2. The method of claim 1, further comprising:
receiving site data from a plurality of clinical sites; and
calculating a higher-level data quality score for the plurality of clinical sites.

3. The method of claim 2, further comprising calculating a second risk indicator based on the higher-level data quality score.

4. The method of claim 2, wherein the plurality of clinical sites comprise sites having a common element.

5. The method of claim 2, wherein the plurality of clinical sites comprise sites from a single country.

6. The method of claim 2, wherein the plurality of clinical sites comprise sites from an entire data study.

7. The method of claim 1, wherein the converting of the site data comprises:
- calculating a plurality of metric values from the site data;
- normalizing each metric value by applying to it a corresponding metric risk profile; and
- aggregating the normalized metric values to calculate the site-level data quality score.

8. The method of claim 7, wherein each metric value is weighted based on significance of the metric to the data quality of the clinical site.

9. The method of claim 1, wherein the risk regions correspond to percentiles of the historic data distribution modified by the ratio.

10. The method of claim 8, wherein the aggregating comprises combining weighted, normalized metric values.

11. The method of claim 8, wherein the weighting applied to each metric value is dynamically determined from site-based feedback concerning actual site data quality conditions.

12. An apparatus, comprising:
a site data filter configured to receive site data from one or more clinical sites, the site data including clinical monitoring data;
a processor configured to:
- convert the site data into a site-level data quality score using at least one single-sided or double-sided metric risk profile, wherein:
  - the site-level data quality score is based on at least two metrics; and
  - the at least one metric risk profile is based on at least clinical study data and historic clinical study data, the clinical study data being received from a plurality of clinical sites and the historic clinical study data having a statistical distribution and a benchmark related to a metric;
- calculate a risk indicator based on the site-level data quality score; and
- generate the at least one metric risk profile in at least substantially real-time by:
  - calculating a clinical study benchmark for at least one of the metrics based on the clinical study data;
  - automatically scaling the historic clinical study data statistical distribution by a ratio of the clinical study benchmark to the historic clinical study data benchmark; and
  - assigning risk regions, utilizing measures of statistical significance, to the scaled statistical distribution; and a component configured to output at least one of said risk indicator and said site-level data quality score.

13. The apparatus of claim 12, wherein:
the site data filter is configured to receive site data from a plurality of clinical sites; and
the processor is configured to calculate a higher-level data quality score for the plurality of clinical sites.

14. The apparatus of claim 13, wherein the processor is configured to calculate a second risk indicator based on the higher-level data quality score.

15. The apparatus of claim 13, wherein the plurality of clinical sites comprise sites having a common element.

16. The apparatus of claim 13, wherein the plurality of clinical sites comprise sites from a single country.

17. The apparatus of claim 13, wherein the plurality of clinical sites comprise sites from an entire data study.

18. The apparatus of claim 12, wherein the processor further comprises a site risk profiler configured to calculate the risk indicator based on the site-level data quality score.

19. The apparatus of claim 12, wherein the processor further comprises:
a site metric processor configured to calculate a plurality of metric values from the site data;
a metric risk profiler configured to normalize each metric value by applying to it a corresponding metric risk profile; and
an aggregator configured to aggregate the normalized metric values to calculate the site-level data quality score.

20. The apparatus of claim 19, wherein each metric value is weighted based on significance of the metric to the data quality of the clinical site.

21. The apparatus of claim 20, wherein the aggregating comprises combining weighted, normalized metric values.

22. The apparatus of claim 20, wherein the weighting applied to each metric value is dynamically determined from site-based feedback concerning actual site data quality conditions.

23. The apparatus of claim 12, wherein the risk regions correspond to percentiles of the historic data distribution modified by the ratio.

24. A computer readable storage medium, comprising computer executable instructions embodied therein, to be executed by a computer, for:
receiving site data from one or more clinical sites, the site data including clinical monitoring data;
converting, by a processor, the site data into a site-level data quality score using at least one single-sided or double-sided metric risk profile, wherein:
- the site-level data quality score is based on at least two metrics; and
- the at least one metric risk profile is based on at least clinical study data and historic clinical study data, the clinical study data being received from a plurality of clinical sites and the historic clinical study data having a statistical distribution and a benchmark related to a metric;

calculating a risk indicator based on the site-level data quality score; and generating, by a processor, the at least one metric risk profile in at least substantially real-time by:
 calculating a clinical study benchmark for at least one of the metrics based on the clinical study data;
 automatically scaling the historic clinical study data statistical distribution by a ratio of the clinical study benchmark to the historic clinical study data benchmark; and
 assigning risk regions, utilizing measures of statistical significance, to the scaled statistical distribution; and outputting at least one of said risk indicator and said site-level data quality score.

25. The computer readable storage medium of claim 24, further comprising computer executable instructions embodied therein, to be executed by a computer, for:
 receiving site data from a plurality of clinical sites; and
 calculating a higher-level data quality score for the plurality of clinical sites.

26. The computer readable storage medium of claim 25, further comprising computer executable instructions embodied therein, to be executed by a computer, for calculating a second risk indicator based on the higher-level data quality score.

27. The computer readable storage medium of claim 24, further comprising computer executable instructions embodied therein, to be executed by a computer, for:
 calculating a plurality of metric values from the site data;
 normalizing each metric value by applying to it a corresponding metric risk profile; and
 aggregating the normalized metric values to calculate the site-level data quality score.

28. The computer readable storage medium of claim 27, wherein each metric value is weighted based on significance of the metric to the data quality of the clinical site.

29. The computer readable storage medium of claim 28, wherein the weighting applied to each metric value is dynamically determined from site-based feedback concerning actual site data quality conditions.

* * * * *